US005972574A

United States Patent [19]

Fischer et al.

[11] Patent Number: 5,972,574

[45] Date of Patent: Oct. 26, 1999

[54] PHOTOGRAPHIC ELEMENT CONTAINING MAGENTA COUPLER HAVING IMPROVED MANUFACTURABILITY AND DYE LIGHT STABILITY

[75] Inventors: Susan M. Fischer; Robert F. Romanet; Daniel L. Kapp; Paul A. Burns; Paul P. Spara, all of Rochester; Rakesh Jain, Penfield; William R. Schleigh, Rochester, all of N.Y.

[73] Assignee: Eastman Kodak Company, Rochester, N.Y.

[21] Appl. No.: 08/784,171

[22] Filed: Jan. 15, 1997

[51] Int. Cl.$^{6}$ .................................................. G03C 7/46

[52] U.S. Cl. .......................... 430/387; 430/558; 430/551

[58] Field of Search .................................. 430/558, 551, 430/387

[56] References Cited

U.S. PATENT DOCUMENTS

| | | | |
|---|---|---|---|
| 5,032,497 | 7/1991 | Nakayama et al. | 430/505 |
| 5,470,697 | 11/1995 | Kita et al. | 430/558 |
| 5,641,613 | 6/1997 | Boff et al. | 430/558 |
| 5,667,952 | 9/1997 | Tang et al. | 430/558 |
| 5,698,386 | 12/1997 | Tang et al. | 430/558 |

FOREIGN PATENT DOCUMENTS

| | | |
|---|---|---|
| 0 704 758 | 7/1987 | European Pat. Off. . |
| 0 602 748 | 3/1990 | European Pat. Off. . |
| 8-166659 | 6/1992 | Japan . |

*Primary Examiner*—Geraldine Letscher
*Attorney, Agent, or Firm*—Arthur E. Kluegel

[57] ABSTRACT

Disclosed is a photographic element comprising a silver halide emulsion layer having associated therewith a dye-forming coupler represented by Formula I:

I

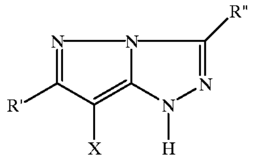

wherein

R" represents the group

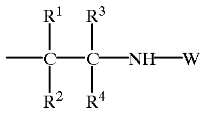

in which $R^1$, $R^2$, and $R^3$ independently selected all groups, provided that any two of $R^1$, $R^2$, and $R^3$ may join to form a ring;

$R^4$ is hydrogen or a substituent, provided that $R^3$ and $R^4$ may join to form a ring when $R^4$ is a substituent; and W is a specified substituent having the formula:

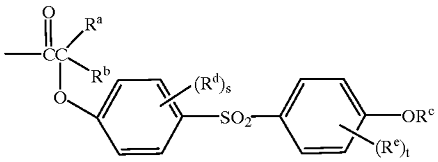

and wherein the remaining substituents are as described in the specification. The use of the coupler of Formula I lends improved manufacturability and dye light stability to the element.

30 Claims, No Drawings

PHOTOGRAPHIC ELEMENT CONTAINING MAGENTA COUPLER HAVING IMPROVED MANUFACTURABILITY AND DYE LIGHT STABILITY

FIELD OF THE INVENTION

This invention relates to a silver halide photographic element and process for its use in which the element contains a particular 1H-pyrazolo[5,1-c]-1,2,4-triazole magenta dye-forming coupler which comprises a ballast having a certain phenylsulfonylphenoxy group in the ballast.

BACKGROUND OF THE INVENTION

Conventional color photography depends on the formation of dyes and uses subtractive primaries to form the desired colors. One of the problems encountered with the dyes which form the images is their tendency to degrade when exposed to light. This is of particular importance with respect to photographic elements intended for direct viewing. Direct view elements include reflective prints and color transmission elements such as motion picture prints and projection slides. Such elements receive substantial exposure to light while being viewed. This not only causes the dye images to fade, but when the dyes of different colors fade at different rates, the image changes color and the neutral areas become undesirably colored. Since the advent of color photography there have been ongoing efforts to improve the dye stability. Nevertheless, there is still a need for further improvement in the dye light stability of photographic elements intended for direct viewing. Efforts have been ongoing to provide stabilized dyes which will exhibit improved light stability. Some of these efforts are described as follows.

EP0 704 758 of Kawagishi et al. teaches certain 1H-pyrazolo[5,1-c]-1,2,4-triazole compounds which are said to be useful for improving color reproduction, color developability, and magenta dye light stability. The coupler contains at the 3-position an aminoalkylene group bonded to a hetero substituted phenyl group by a —C(O)—, —$SO_2$—, —$SO_2$NR—, —C(O)NR—, or —COOR— group. Neither the carbon of the aminoalkylene group alpha or beta to the azole ring to which it is bonded is required to be further substituted. Among the specific couplers contemplated are those having, for example, α-methyl, α-isopropyl, α-ethyl, α-dodecyl, α-phenyl and α,α-dimethyl links to the azole ring. In almost every example, the α carbon is linked directly to a heterogroup of the substituent. When there is present a β-carbon, it is never further substituted.

EP 602 748 of Tang et al. suggests generic substituent groups for pyrazolotriazole couplers which enhance the combination of color reproduction, dye light stability and coupler reactivity. It is stated that substitution at the alpha carbon is desired, but there is no specific suggestion that further substitution at the beta carbon is advantageous.

U.S. Pat. No. 5,470,697 of Kita et al. suggests pyrazolotriazole couplers having a fully substituted carbon in the alpha position with an oxygen linked moiety in two of the branches for purposes of improved sensitivity and reduced development pH sensitivity No data on dye stability is given and there is no recognition of the advantage of any particular substituent combination for purposes of improving dye light stability.

U.S. Pat. No. 5,032,497 of Nakayama et al. suggests a certain pyrazolotriazole coupler having a tertiary alkyl group in the 3-position and a primary alkyl group in the 6-position for the purpose of improving the absorption spectra of the magenta dye formed upon development and improving the resistance of the dye to formaldehyde and light.

In addition to the desired light stability of the resulting magenta dye, it is also important that the magenta coupler be manufacturable in a commercial sense. Purification is an integral part of the synthesis of compounds. There are many methods of purification known in the art such as crystallization, distillation, chromatography, and dialysis. These methods find wide application in academia and in industry. Many of these methods, however, are limited in that they can handle only relatively small amounts of material. For example, chromatography is an extremely efficient method of purification of organic compounds but when applied to quantities over 25 grams, the quantities of absorbent, the volumes of solvents needed, and the physical operations required (such as evaporation of elutant solvents), make the operation impractical for large quantities from a cost point of view.

Solids have another advantage during manufacture. Compounds need to be transferred between reaction vessels and between areas of manufacture and areas of use (such as dispersion making in the case of photographic couplers). The transfer of liquids and oils, especially high molecular weight materials which tend to be very viscous, can be problematic. The transfer of solids is easier.

For the manufacture of large amounts of material, it is highly desirable to use purification techniques that are cost effective for large amounts of material. For the manufacture of photographic couplers, hundreds of kilograms a year or more would be needed and thus a purification method such as chromatography as described above would be impractical. The two practical methods of purification in the manufacture of large amounts of material are distillation and recrystallization. In order to use distillation, the material must boil at temperatures less than 140° C. at reduced pressure. Photographic couplers are typically too high boiling to distill, and therefore recrystallization is the only practical way to purify large quantities of such materials.

In order to purify materials by recrystallization, it is necessary that the materials have a well defined crystal structure. Materials having this well defined crystal structure are characterized by a sharp melting point when pure; the melting point range is typically less than 2° C. A discussion of recrystallization can be found in *Purification of Laboratory Chemicals* by D. D. Perrin and W. L. F. Armarego, Pergamon Press, N.Y. 1988.

Thus it is a problem to be solved to provide a magenta coupler that not only forms a dye having advantageous resistance to light degradation but, from the practical standpoint, one that is crystallizable in order to be capable of industrial exploitation.

SUMMARY OF THE INVENTION

The invention provides a photographic element comprising a silver halide emulsion layer having associated therewith a dye-forming coupler represented by Formula I:

I

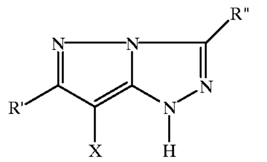

wherein

X is hydrogen or a coupling-off group; and

R' is a tertiary alkyl group and R" represents the group

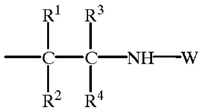

in which $R^1$, $R^2$, and $R^3$ are independently selected alkyl groups, provided that any two of $R^1$, $R^2$and $R^3$ may join to form a ring;

$R^4$ is hydrogen or a substituent, provided that $R^3$ and $R^4$ may join to form a ring when $R^4$ is a substituent; and W is a substituent having the formula:

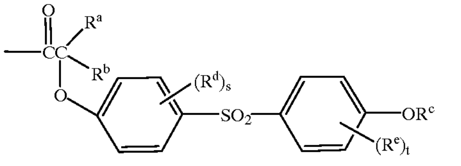

wherein $R^a$ and $R^b$ are independently selected from the group consisting of hydrogen, and alkyl or aryl groups;

$R^c$ is a substituent;

each $R^d$ and $R^e$ is an independently selected substituent with s and t being independently selected integers from 0 to 4.

The invention also provides a process for forming an image in the element of the invention.

The use of the coupler of Formula I lends improved manufacturability and dye light stability to the magenta coupler of the element.

DETAILED DESCRIPTION OF THE INVENTION

The invention provides a photographic element comprising a silver halide emulsion layer having associated therewith a dye-forming coupler represented by Formula I:

I

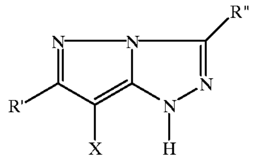

wherein

X is hydrogen or a coupling-off group; and

R' is a tertiary alkyl group and R" represents the group

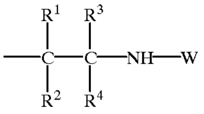

in which $R^1$, $R^2$, and $R^3$ are independently selected alkyl groups, provided that any two of $R^1$, $R^2$, and $R^3$ may join to form a ring;

$R^4$ is hydrogen or a substituent, provided that $R^3$ and $R^4$ may join to form a ring when $R^4$ is a substituent; and W is a substituent having the formula:

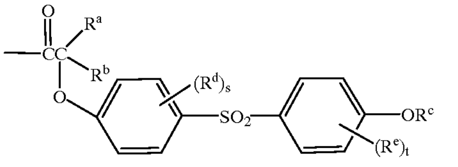

wherein $R^a$ and $R^b$ are independently selected from the group consisting of hydrogen, and alkyl or aryl groups;

$R^c$ is a substituent;

each $R^d$ and $R^e$ is an independently selected substituent with s and t being independently selected integers from 0 to 4.

The magenta coupler useful in the invention is termed a 1H-pyrazolo[5,1-c]-1,2,4-triazole compound. Substituent R' of the coupler is suitably any tertiary alkyl group. Suitable examples include 1-methyl-1-cyclopropyl, t-butyl, t-octyl, [2.2.2]tricyclooctyl, and adamantyl t-Butyl is generally suitable.

In substituent R", $R^1$, $R^2$, and $R^3$ are independently selected alkyl groups. Suitably they each contain from 1 to 20 carbon atoms, often 6 or less carbons. Typically, methyl, ethyl, propyl, isopropyl or dodecyl groups are employed. It is suitable to have $R^1$ and $R^2$ join to form cycloalkyl groups such as cyclopropyl, cyclobutyl, cyclopentyl, cyclohexyl, etc.

It is generally preferred that $R^4$ be a substituent rather than hydrogen. $R^4$ may suitably be an alkyl, aryl or acyl group. Suitably, $R^4$ will have from 1 to 20 carbon atoms and is preferably an alkyl group. Also useful are phenyl groups such as phenyl, methoxyphenyl, methylsulfonamidophenyl, or tolyl and naphthyl groups.

In one embodiment of the invention, $R^1$ through $R^4$ are each independently selected unsubstituted alkyl groups. In another embodiment they are each unsubstituted methyl groups.

The group W is a substituent of the formula:

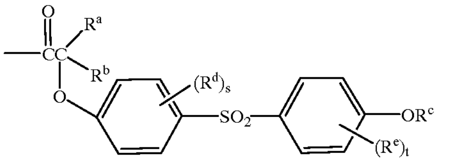

$R^a$ and $R^b$ are independently selected from hydrogen, alkyl groups or aryl groups. Suitably, $R^a$ will be an alkyl or aryl group, conveniently an alkyl group and $R^b$ will be hydrogen, or an alkyl or aryl group. Suitably $R^a$ and $R^b$ are independently selected from a phenyl group or an alkyl group having up to 30 carbon atoms such as methyl, ethyl, propyl, isopropyl, butyl, hexyl, cyclohexyl, octyl, decyl, hexadecyl, etc. $R^a$ is one possible location for a ballast group which will serve to render the coupler nondiffusing in the emulsion layer. For this purpose, the alkyl group will typically contain at least 6 or more carbon atoms. It is provided that $R^a$ and $R^b$ may join to form a ring such as a cyclopentyl ring.

$R^c$ is a substituent and is suitably an alkyl or aryl group. Arylalkyl groups such as phenylmethylene groups are useful. If desired, this group may perform some or all of the ballasting required of the coupler. If it supplies all of the ballast it will contain 6 or more carbon atoms and suitably 10 or more carbon atoms.

Each $R^d$ and $R^e$ is an independently selected substituent with s and t being independently selected integers from 0 to 4. Examples of suitable substituents are alkyl, aryl, alkoxy, aryloxy and halogen groups.

The $R^a$ through $R^e$ substituents may also be selected so as to improve the activity of the coupler. Solubilizing groups such as hydroxyl, sulfonamide, and carboxyl groups are examples of suitable such groups.

The photographic element of the invention is most typically a color print element in which the light sensitive layers are provided on a paper or other reflective support. Such materials are suitably developed using the presently employed Kodak RA-4 process. Alternatively, the element may be comprised of a transparent film support suitable for projection viewing.

The following are examples of couplers of the invention. (Hereafter, "tBu" represents tertiary butyl, "Et" represents ethyl, "Me" represents methyl, and "Ac" represents acetyl.)

M-1

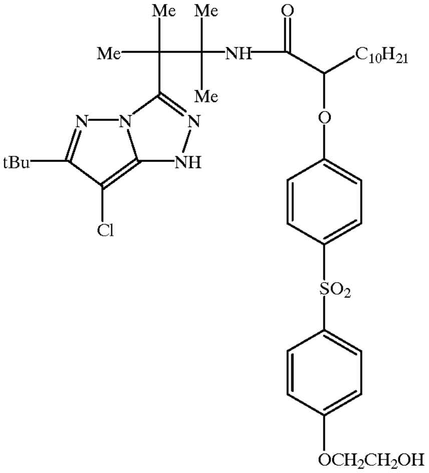

-continued

M-2

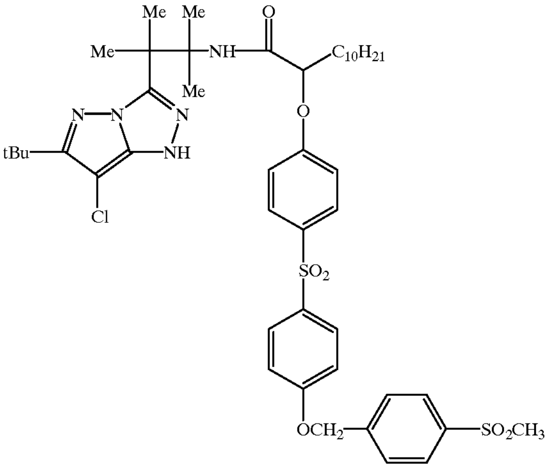

M-3

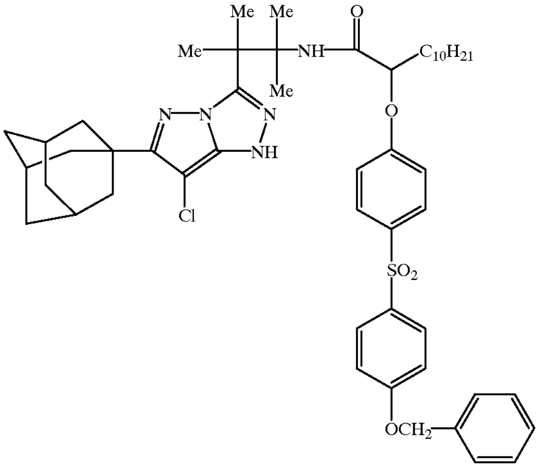

M-4

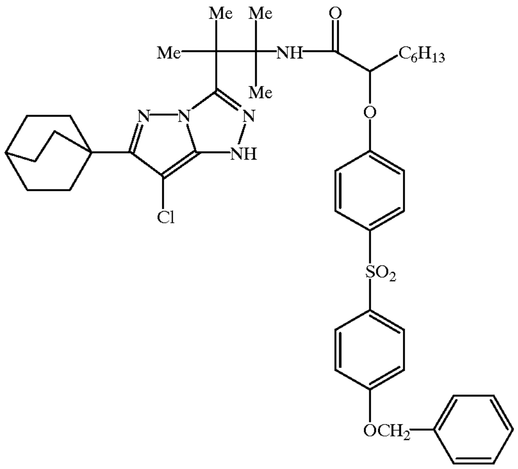

-continued
M-5
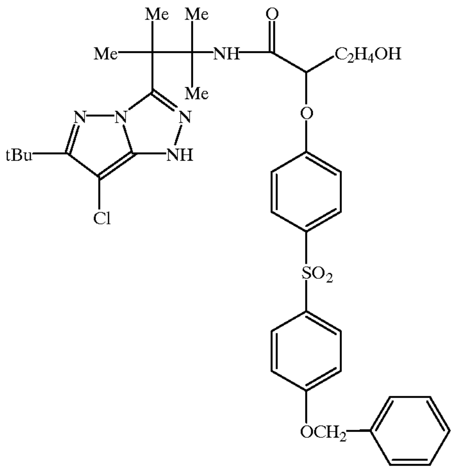
M-6
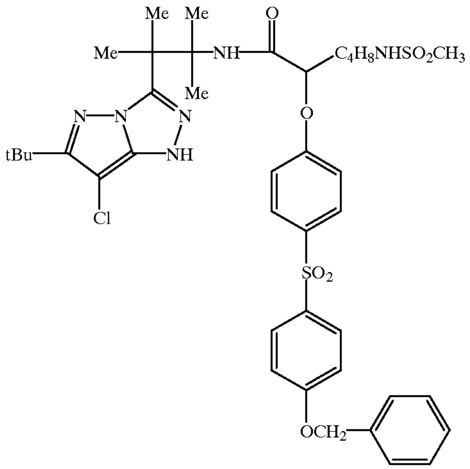
M-7
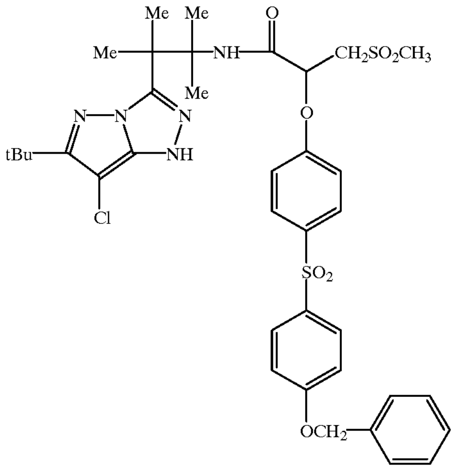
-continued
M-8
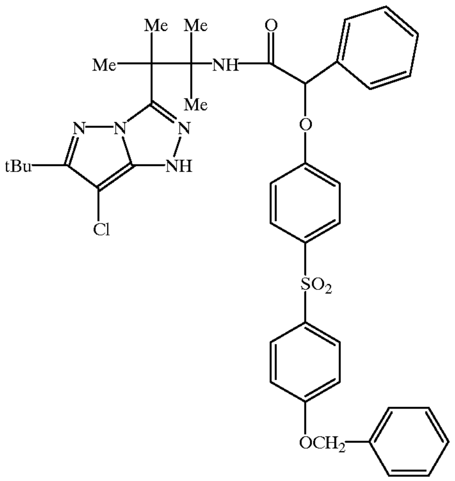
M-9
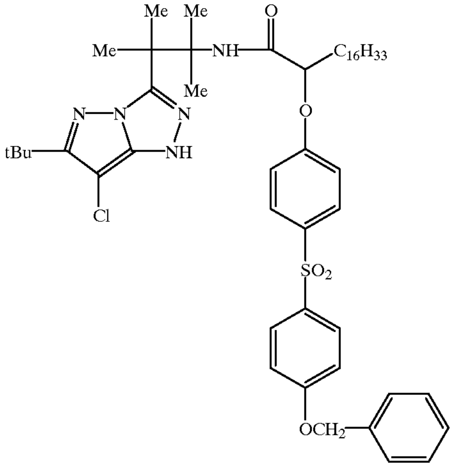
M-10
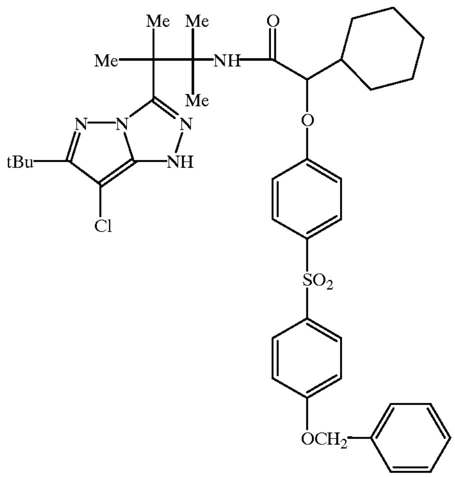

-continued
M-11
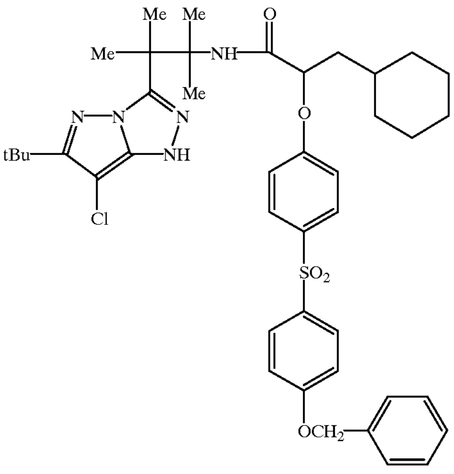
M-12
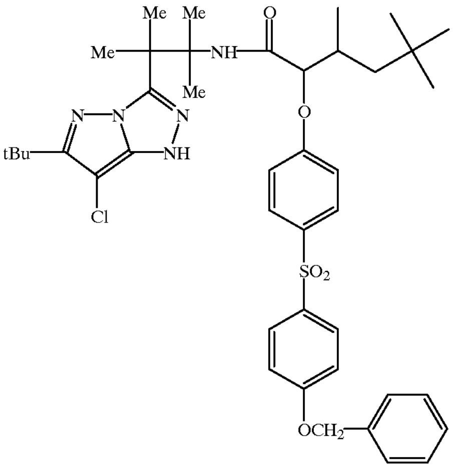
M-13
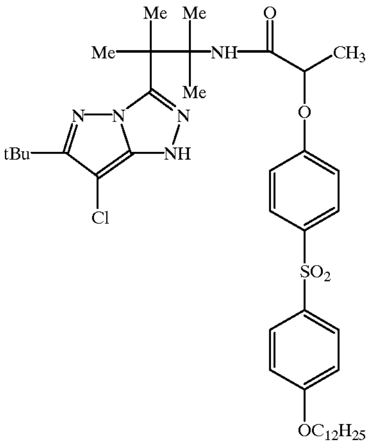
-continued
M-14
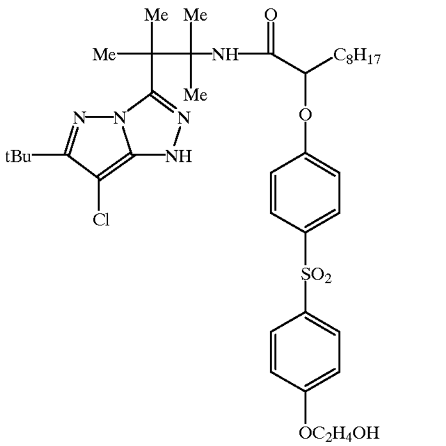
M-15
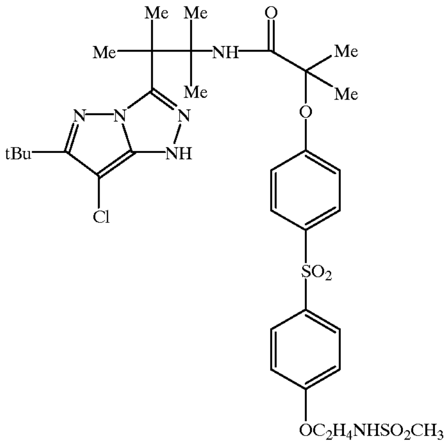
M-16
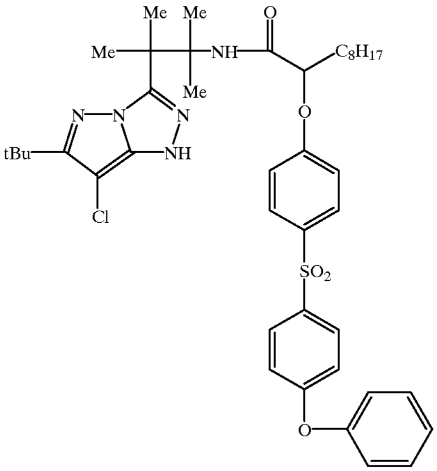

-continued
M-17
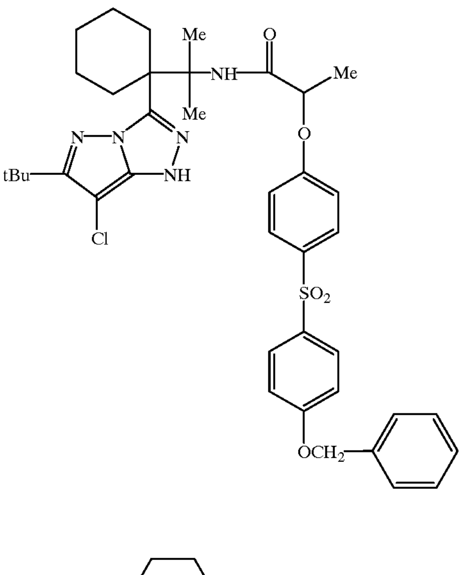
M-18
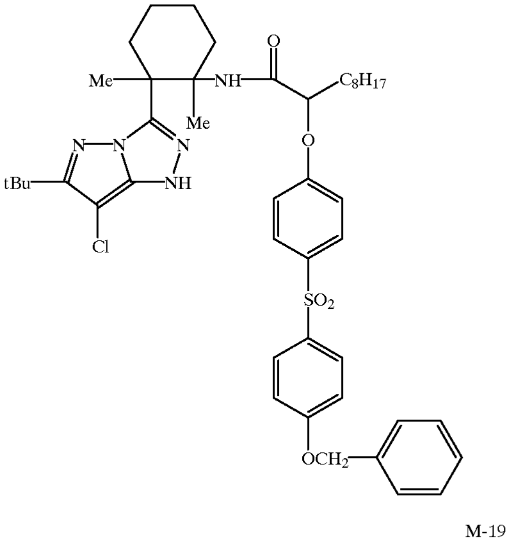
M-19
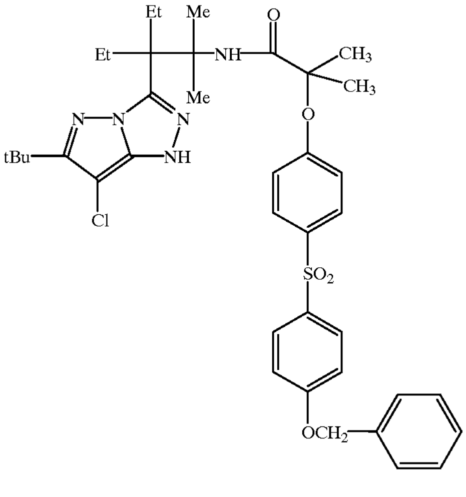
-continued
M-20
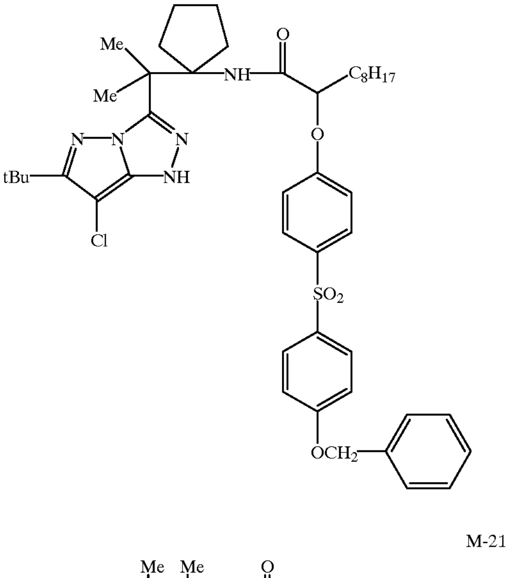
M-21
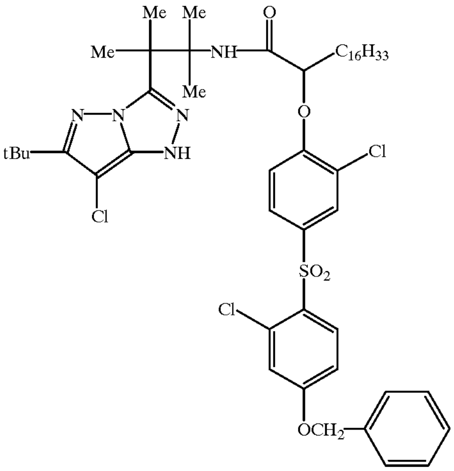
M-22
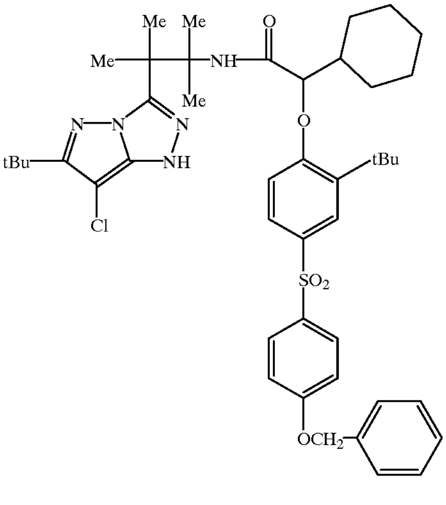

-continued
M-23
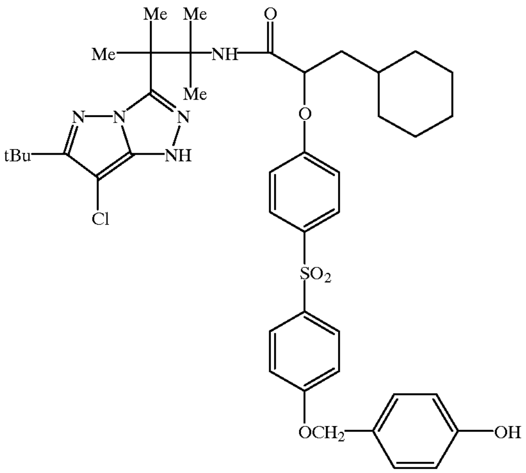
M-24
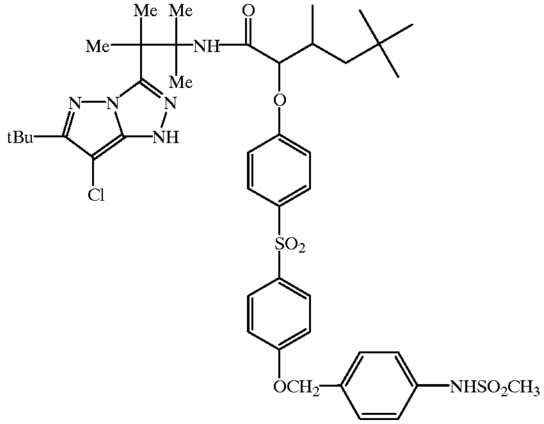
M-25
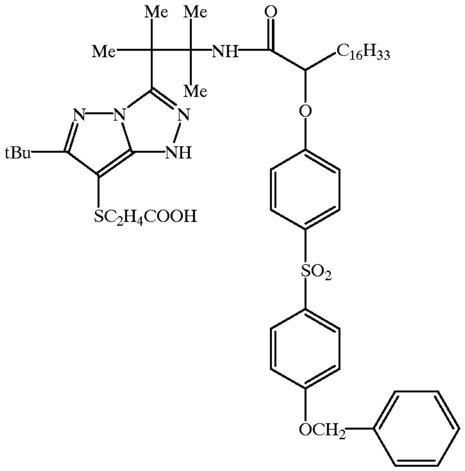
-continued
M-26
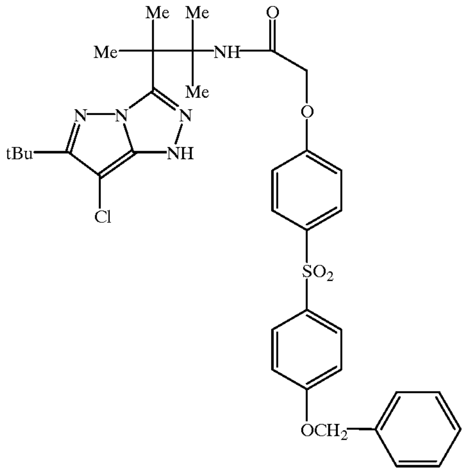
M-27
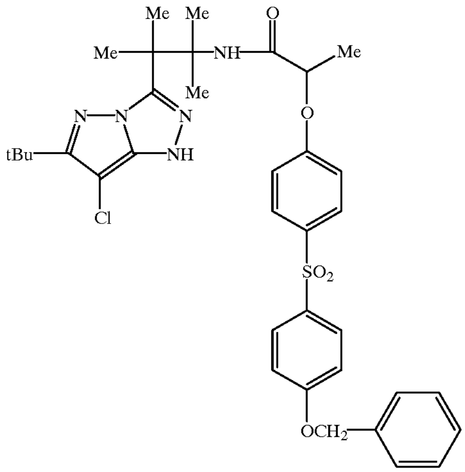
M-28
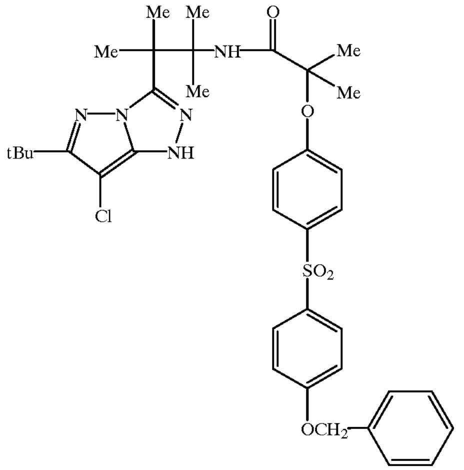

-continued
M-29
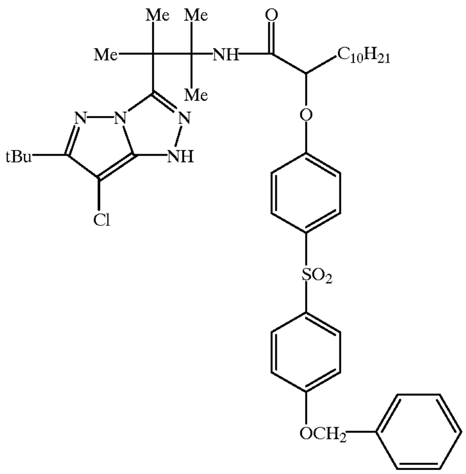
M-30
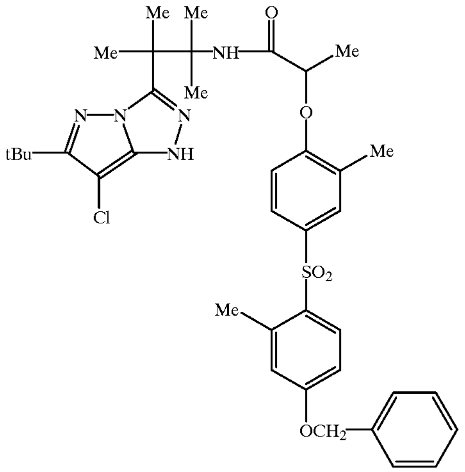
M-31
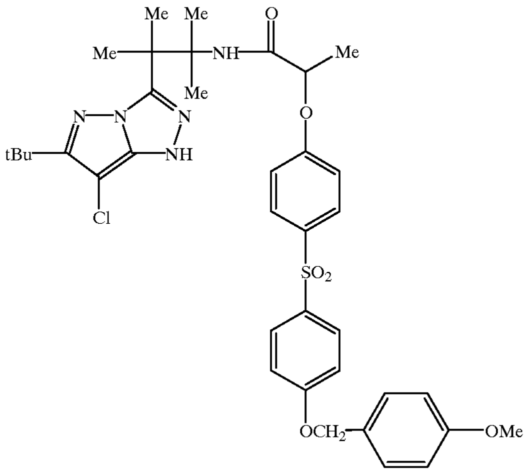
-continued
M-32
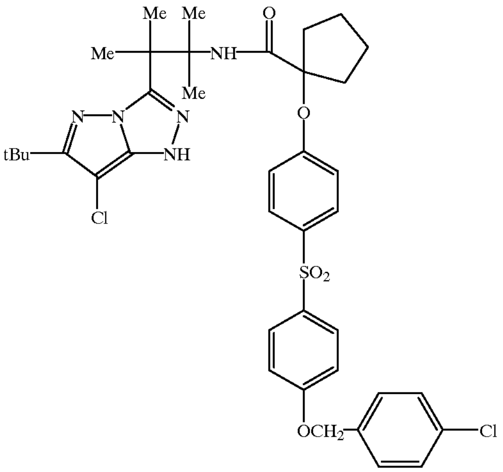
M-33
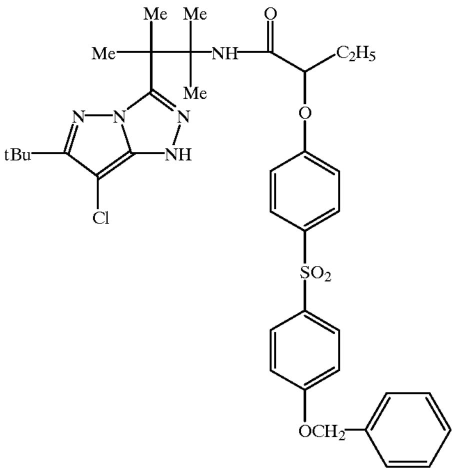
M-34
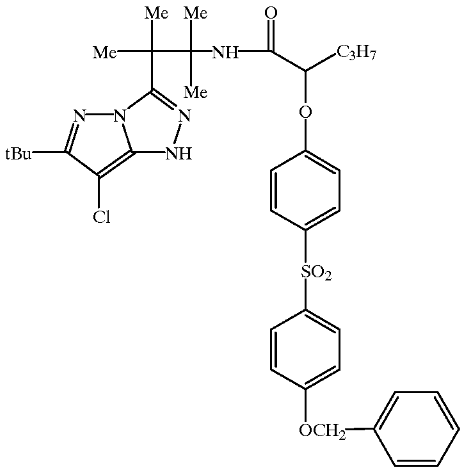

-continued
M-35
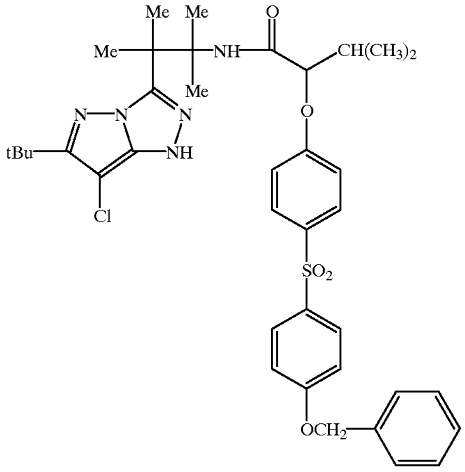
M-36
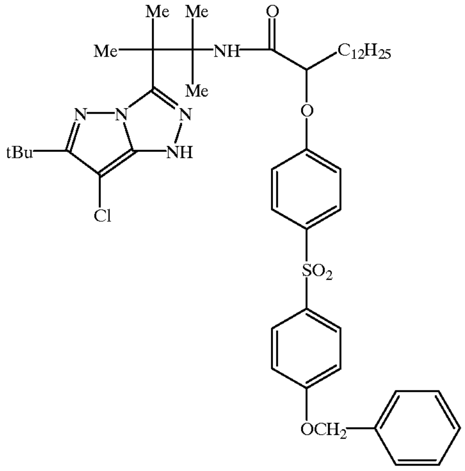
To further enhance the light stability of the dyes formed from the couplers of the invention, it is generally desired to include one or more stabilizing compounds. The following are examples of stabilizing compounds.
St-1
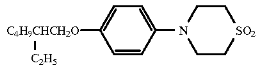
St-2
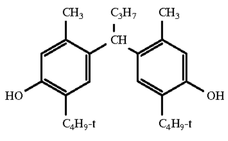
St-3
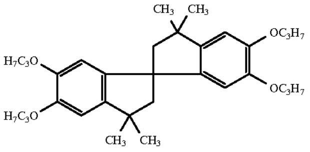
-continued
St-4
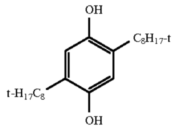
St-5
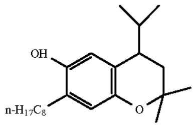
St-6
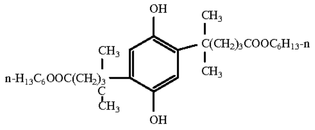
St-7
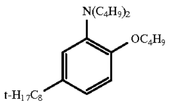
St-8
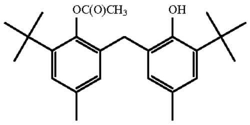
St-9
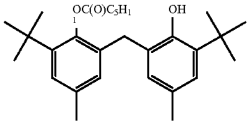
St-10
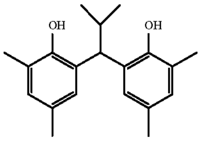
St-11
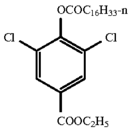
St-12
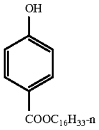
St-13
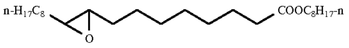

-continued

St-14

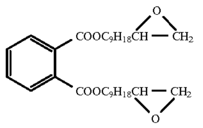

St-15

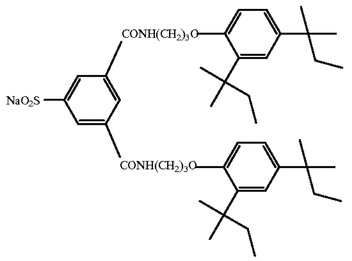

St-16

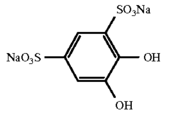

St-17

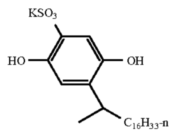

St-18

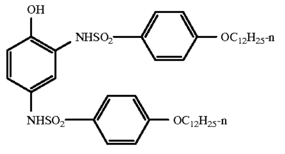

St-19

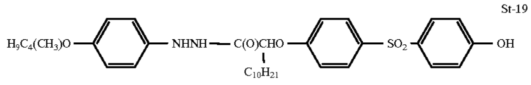

St-20

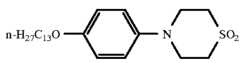

St-22

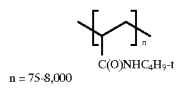

and

St-23

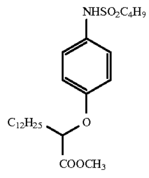

The stabilizers represented by generic formulas St-I, St-II, and St-III have been found suitable for use with the couplers used in the invention.

St-I

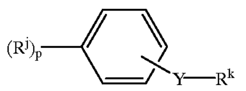

St-II

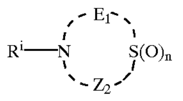

and

St-III

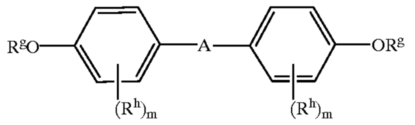

In the formulas:

each $R^g$ independently represents a hydrogen atom, an alkyl group, an alkenyl group or an aryl group;

each $R^h$ independently represents a halogen atom, an alkyl group, an alkenyl group, an alkoxy group, an aryl group, an aryloxy group, an alkylthio group, an aryl thio group, an acyl group, an acylamino group, a sulfonyl group, a sulfonamide group or a hydroxy group;

each m is, individually an integer of 0 to 4; and

A represents a branched or unbranched alkylene group having 1 to 6 carbon atoms in its linear structure extending between the phenoxy rings, $R^i$ represents an aryl group or a heterocyclic group;

$Z_1$ and $Z_2$ each represent an alkylene group having 1 to 3 carbon atoms provided that the total number of carbon atoms in the ring is 3 to 6;

n is an integer of 1 or 2;

each $R^j$ is independently alkyl or alkoxy of 1 to 32 carbon atoms;

p is an integer of 1 to 4 and when p is greater than 1, only one $R^j$ is alkoxy;

Y is $—NHSO_2—$ or $—SO_2NH—$; and $R^k$ is an alkyl group of 1 to 16 carbon atoms.

Suitable compounds within these formulas are more fully described in U.S. Pat. No. 5,561,037.

In one embodiment, a compound within St-I and one within St-II are incorporated with the coupler and in another embodiment, three compounds from within each of the three formulas may be employed. Stabilizer St-23, St-1, and St-2 may be employed as species of St-I, St-II, and St-III, respectively.

Typically, the couplers and the stabilizers with which they are associated are dispersed in the same layer of the photographic element in a high boiling organic compound known in the art as a coupler solvent. Representative coupler solvents include phthalic acid alkyl esters such as diundecyl phthalate, dibutyl phthalate, bis-2-ethylhexyl phthalate, and dioctyl phthalate, phosphoric acid esters such as tricresyl phosphate, diphenyl phosphate, tris-2-ethylhexyl phosphate, and tris-3,5,5-trimethylhexyl phosphate, citric acid esters such as tributyl acetylcitrate, 2-(2-butoxyethoxy)ethyl acetate, and 1,4-cyclohexyldimethylene bis(2- ethylhexanoate), benzoic acid esters such as octyl benzoate, aliphatic amides such as N,N-diethyl lauramide, N,N-diethyldodecanamide, N,N-dibutyldodecanamide, mono and polyvalent alcohols such as oleyl alcohol and glycerin monooleate, and alkyl phenols such as p-dodecyl phenol and 2,4-di-t-butyl or 2,4-di-t-penyl phenol. Commonly used coupler solvents are the phthalate esters, which can be used alone or in combination with one another or with other coupler solvents. Selection of the particular coupler solvent has been found to have an influence both on the activity of the coupler and the hue of the dye formed on coupling.

Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido,p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfmyl, such as methylsulfinyl, octylsulfinyl, 2-ethylhexylsulfinyl, dodecylsulfmyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3- to 7-membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 42 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arysulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive dsilver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Scan facilitating is described in Section XIV. Supports, exposure, development systems, and processing methods and agents are described in Sections XV to XX. Certain desirable photographic elements and processing steps are described in *Research Disclosure*, Item 37038, February 1995, and desirable features for color prints are described in *Research Disclosure*, Item 18716, November 1979.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl such as oxazolidinyl or hydantoinyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006,755A and 2,017,704A, the disclosures of which are incorporated herein by reference.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895,826, 3,002,836, 3,034,892, 3,041,236, 4,333,999, 4,883,746 and "Farbkuppler-eine LiteratureUbersicht," published in Agfa Mitteilungen, Band III, pp. 156–175 (1961). Preferably such couplers are phenols and naphthols that form cyan dyes on reaction with oxidized color developing agent.

Couplers that form magenta dyes upon reaction with oxidized color developing agent are described in such representative patents and publications as: U.S. Pat. Nos. 2,311,082, 2,343,703, 2,369,489, 2,600,788, 2,908,573, 3,062,653, 3,152,896, 3,519,429, 3,758,309, 4,540,654, and "Farbkuppler-eine LiteratureUbersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized and color developing agent are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine LiteratureUbersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: U.K. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629.

The invention materials may be used in association with materials that accelerate or otherwise modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784, may be useful. Also contemplated is use of the compositions in association with nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the compositions may be blocked or coated in protected form as described, for example, in Japanese Application 61/258,249 or U.S. Pat. No. 5,019,492.

The invention materials may further be used in combination with image-modifying compounds such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

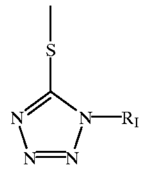

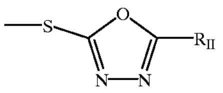

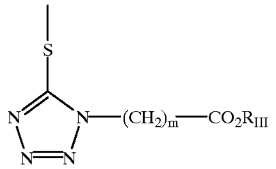

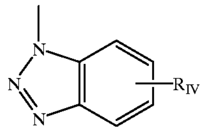

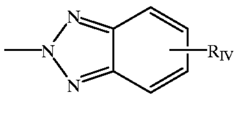

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. Nos. 4,409,323; 4,421,845; Japanese Applications 57-188035; 58-98728; 58-209736; 58-209738) groups utilizing ester hydrolysis (German Patent Application (OLS) No. 2,626,315; groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

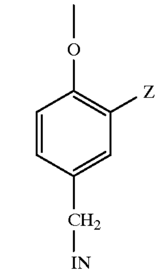

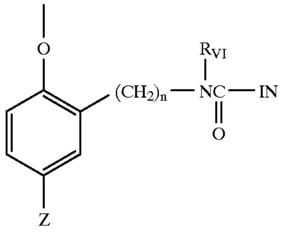

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

D1

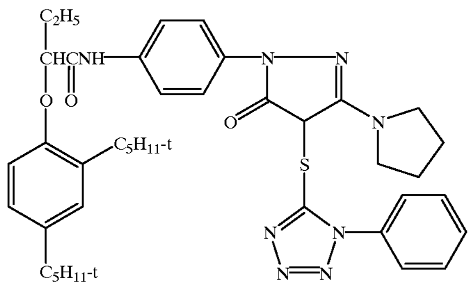

D2

-continued

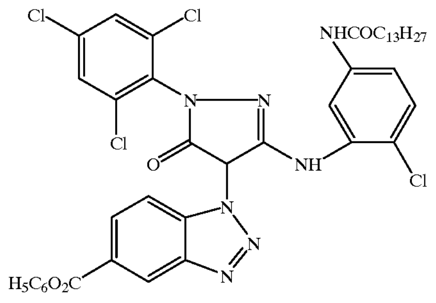

D3

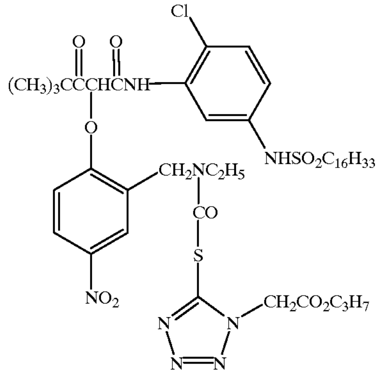

D4

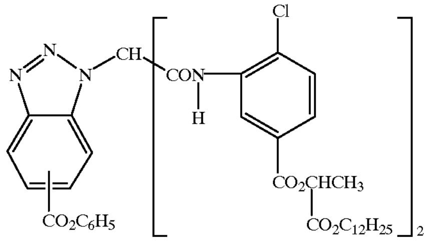

D5

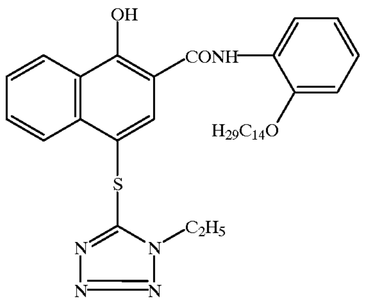

D6

-continued
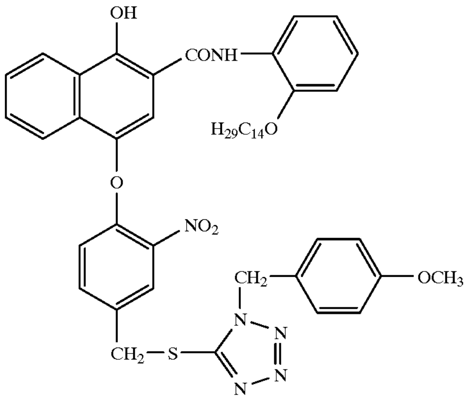
D7
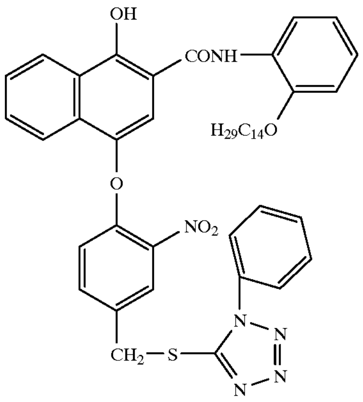
D8
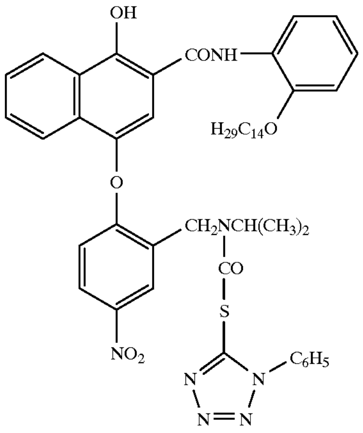
D9
-continued
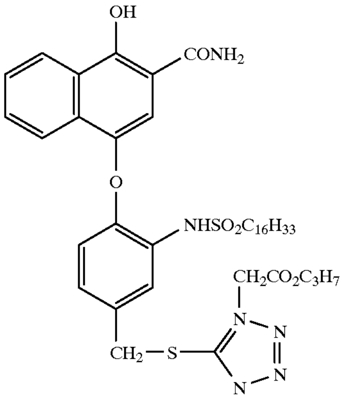
D10
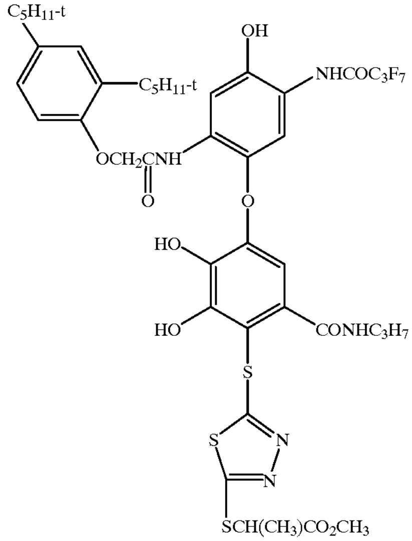
D11
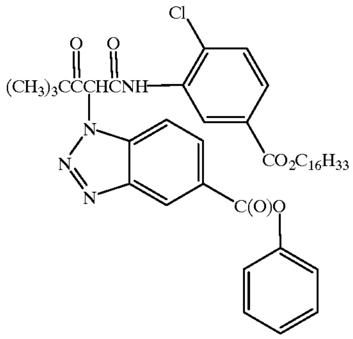
D12

-continued

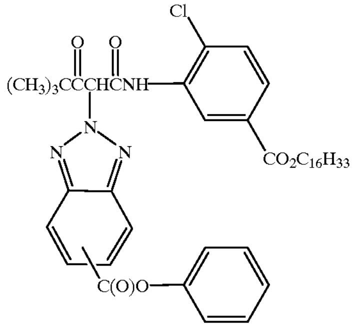

Useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.06 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions are negative-working emulsions, such as surface-sensitive emulsions or unfogged internal latent image-forming emulsions.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. One type of such element is designed for image capture, and speed (the sensitivity of the element to low light conditions) is usually critical to obtaining sufficient image in such elements. When such elements are to be subsequently used to optically generate a color print, they are provided on a transparent support. They may then be processed, for example, in known color negative processes such as described in The British Journal of Photography Annual of 1988, pages 191–198. If such an element is to be employed to generate a viewable projection print as for a motion picture, a process such as the Kodak ECN-2 process described in the H-24 Manual available from Eastman Kodak Co. may be employed to provide the print on a transparent support. Color negative development times are typically 3' 15" or less and desirably 90 or even 60 seconds or less.

Elements destined for color reflection prints are provided on a reflective support and may be exposed via optical negative/positive printing and processed, for example, using the Kodak RA-4 process as described in The British Journal of Photography Annual of 1988, Pp 198–199; color projection prints may be processed, for example, in accordance with the Kodak ECP-2 process as described in the H-24 Manual. Reflective color prints are typically provided using silver halide emulsions containing 99% or more of silver chloride, and development times are typically 90 seconds or less and desirably 45 or even 30 seconds or less.

To provide a positive (or reversal) image, the color development step can be preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as the Kodak E-6 process. Alternatively, a direct positive emulsion can be employed to obtain a positive image.

The above emulsions are typically sold with instructions to process using the appropriate method such as the mentioned color negative (Kodak C-41), color print (Kodak RA-4), or reversal (Kodak E6) process.

Preferred color developing agents are p-phenylenediamines such as:

4amino-N,N-diethylaniline hydrochloride, 4-amino-3-methyl-N,N-diethylaniline hydrochloride, 4-amino-3-methyl-N-ethyl-N-(2-methanesulfonamidoethyl)aniline sesquisulfate hydrate, 4-amino-3-methyl-N-ethyl-N-(2-hydroxyethyl)aniline sulfate, 4-amino-3-(2-methanesulfonamidoethyl)-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The coupler of the invention is readily prepared through conventional techniques. The following will demonstrate a suitable method.

Synthetic Example-Coupler M-29

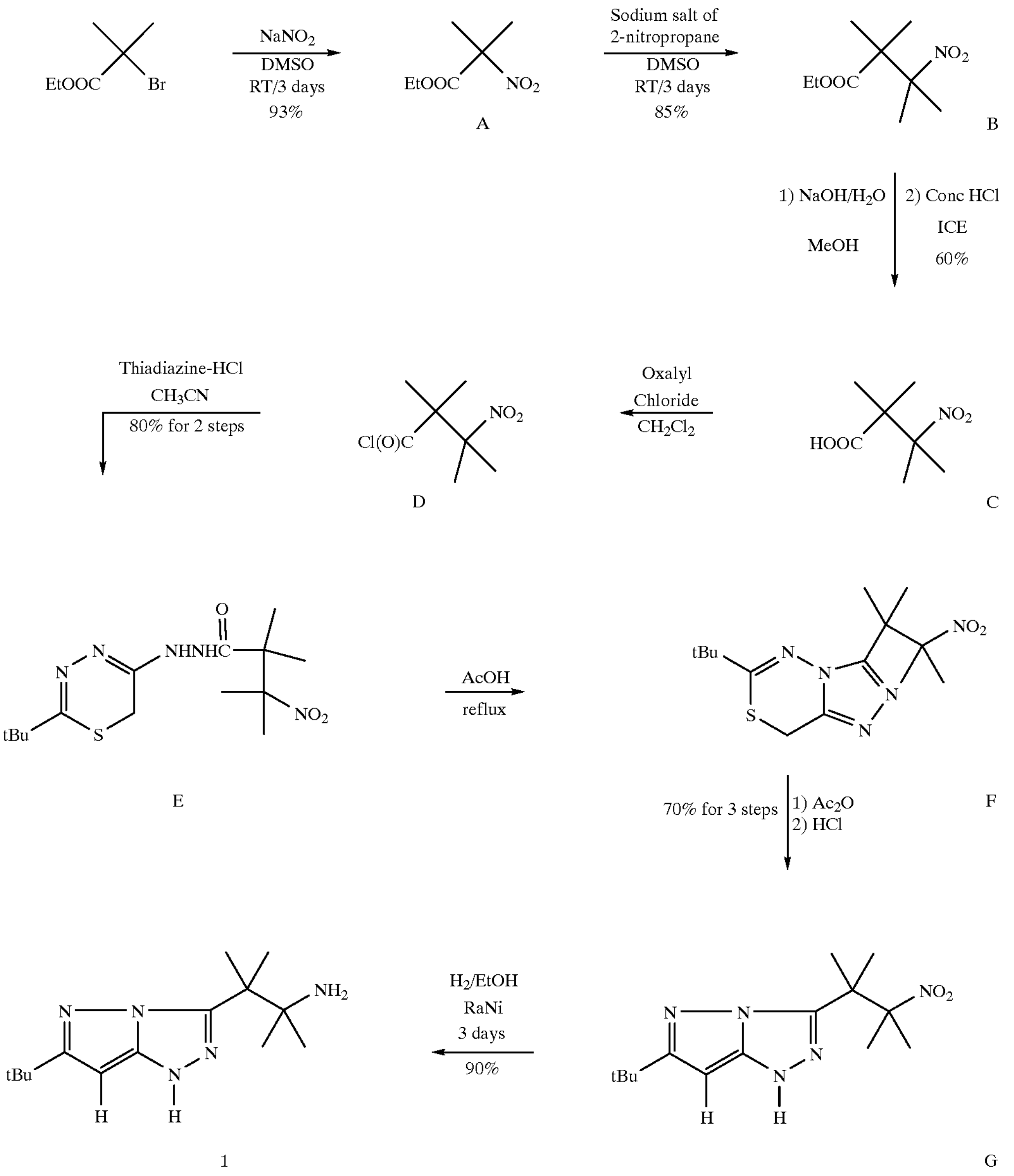

-continued

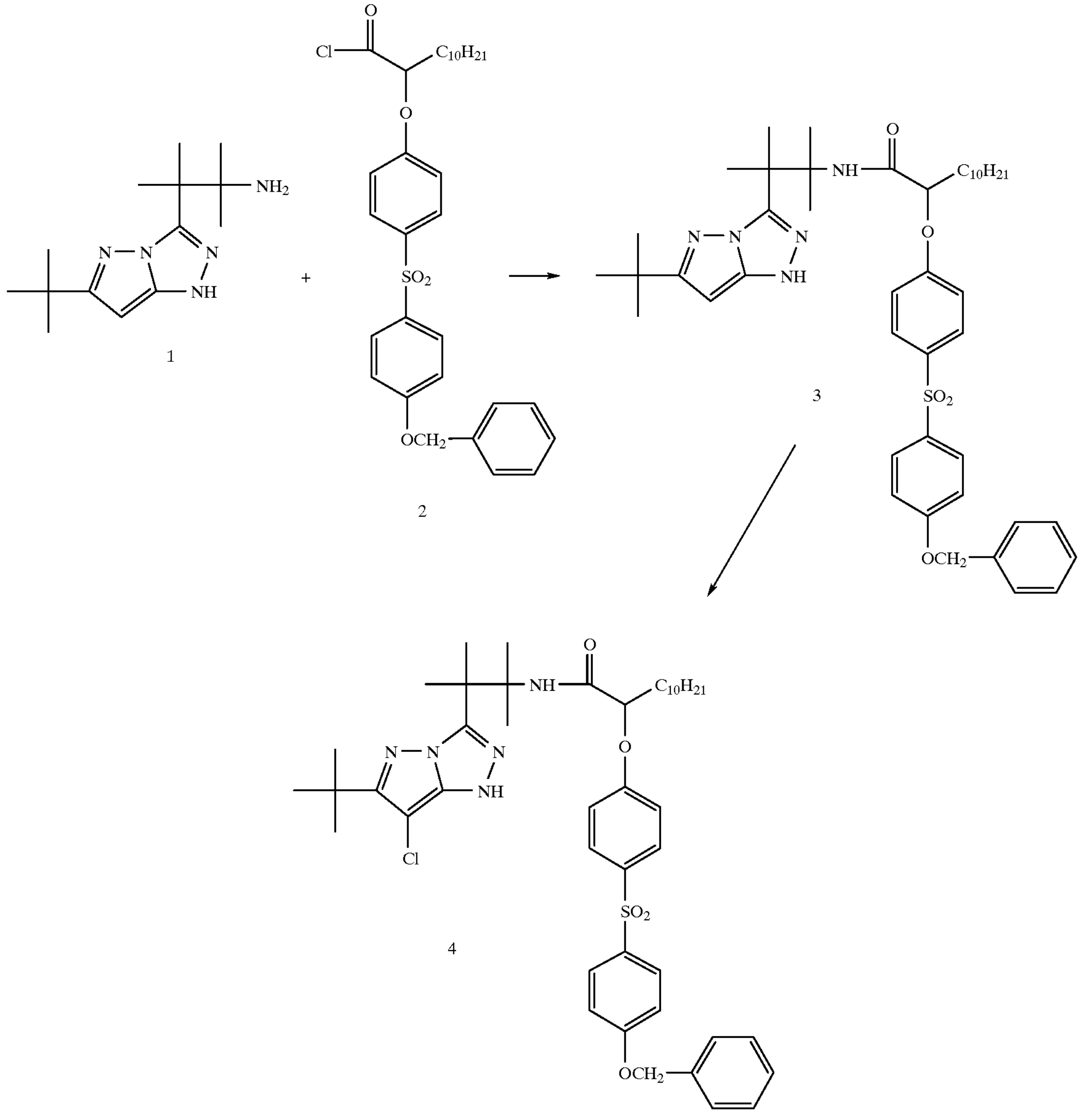

1

2

3

4

M-29

Synthesis of Compound A (Ethyl alpha nitro isobutyrate)

Sodium nitrate 36 g (0.52 mol) was dissolved in 600 ml of dimethylformamide and the ethyl bromoisobutyrate (58.5 g, 0.3 mol) was added in one portion and the reaction was stirred overnight at room temperature. The reaction was partitioned with diethyl ether and water. The aqueous layer was extracted with additional ether and the combined ether layers were washed with water. The ether was dried with $MgSO_4$, and concentrated to yield 42 g (87%) of the desired nitro compound. (See N. Kornblum, JACS (1957), vol. 79, p2507.)

Synthesis of Compound B

The sodium salt of nitropropane was prepared from adding 1 equiv. of nitropropane with rapid stirring to a solution of sodium methoxide (1 equiv.) in methanol. The solution is concentrated to a white solid.

Compound A (40 g, 0.24 mol) was dissolved in DMSO (500 ml) and treated with the nitropopane sodium salt and stirred at room temperature with a UV lamp probe in a sleeve inside the flask for 12 hours. (The use of a light source reduces the reaction time by a factor of 3 to 5.) The reaction was partitioned between water and ligroin. The organic layer was washed with water, dried with $MgSO_4$ and concentrated to yield 44 g (90%) of the desired compound 2.

Synthesis of Compound C (Hydrolysis of Compound B)

Compound B (40 g, 0.2 mol) was mixed with methanol (300 ml) and with sodium hydroxide (40 g of 50% by weight, 0.5 mol) and water (100 ml) and tetrabutylammonium sulfate (2 g) and heated at reflux for 3 days. The reaction was concentrated to remove methanol and extracted with ethyl acetate for remove any unreacted ester. Ice was added to the aqueous layer and a mixture of conc. HCl (42 ml, 0.5 mol) and ice was added carefully. (Note: rapid decarboxylation occurs if the solution warms to room temperature). A white solid is collected, washed with water, and dried to give 22 g (63%) of compound C.

Synthesis of Acid Chloride Compound D

The carboxylic acid compound C (20 g, 0.11 mol) was mixed with dichloromethane (150 ml) and treated with oxalyl chloride (13 ml, 0.15 mol) and a few drops of dimethylformamide. The reaction was stirred at room temperature for 3 hr and concentrated.

Synthesis of Compound E

The hydrazinothiadiazine hydrochloride salt (24 g, 0.11 mol) was mixed with acetonitrile (300 ml) and triethylamine (11 g, 0.11 mol) and stirred at room temperature for 15 min. The acid chloride compound D was dissolved in 20 ml of acetonitrile and added dropwise to the thiadiazine mixture. The reaction was stirred overnight and concentrated to a solid. The solid was partitioned between EtOAc and sat'd $NaHCO_3$ (tetrahydrofuran was added to the organic layer to keep the product from crystallizing out). The organic layer was dried and conc. to yield 27 g (71%) of compound E.

Synthesis of Compound F

Compound E (20 g, 0.06 mol) was mixed with acetic acid (100 ml) and heated at reflux for 24 hr. The reaction was diluted with water and a solid was collected. The solid was washed with water and dried to yield 16 g (84%) of compound F.

Synthesis of Compound G

Compound F (10 g, 0.03 mol) was mixed with acetic anhydride (100 ml) and heated at reflux for 24 hr. The reaction was cooled to room temperature and carefully treated with conc. HCl (95 ml). The reaction was heated at 60° C. for one hour and partitioned between EtOAc and water. The organic layer was washed with sat'd $NaHCO_3$ until neutralized. The organic layer was dried and concentrated to a solid. The solid was crystallized from heptane to yield 7 g (77%) of product.

Synthesis of Compound 1

The nitro compound G (6 g) was dissolved in ethanol and treated with 6 g of Rainey nickel and shaken with hydrogen at room temperature for 48 hr. The reaction was filtered and concentrated to a thick oil which was carried on.

Synthesis of Coupler M-29

4.24 gm of 1 were dissolved in 150 ml of dry THF and cooled in an ice bath. 2.7 ml (1.2 equiv.) triethylamine added followed by 9.78 gm (1.1 equiv.) ballast acid chloride 2 dissolved in a small amount of THF. The ice bath was removed and the reaction stirred for 3 hours. 20 ml of a 0.5M solution of sodium methoxide in methanol was added and stirred 15 minutes. The mixture was added to dilute HCl and ethyl acetate added. After shaking, the organic layer was separated and washed two times with water, dried with $MgSO_4$ and evaporated to 11.1 gm yellow oil 3. The oil was dissolved in 100 ml of THF and 2.1 gm (1.1 equiv.) of N-chloro-succinimide was added. After 5 minutes, 5 ml of a 10% solution of $Na_2S_2O_4$ was added and stirred vigorously for 10 minutes. The mixture added to a mixture of ethyl acetate and water, shaken, the water separated, the organic layer washed two times, dried over $MgSO_4$ and evaporated to a yellow oil. The product was crystallized from acetonitrile to yield M-29 (4) melting at 130–132°.

Crystallinity Examples

Various 1H-pyrazolo[5,1-c]-1,2,4-triazole magenta dye-forming coupler compounds were prepared in an effort to determine whether such compounds were crystalline in nature. As explained in the Background of the Invention, crystalline materials melt over a very narrow temperature range of several degrees while noncrystalline materials are either not solids to begin with or melt over a much broader temperature range.

The following compounds were prepared in accordance with the above scheme and found to be crystalline.

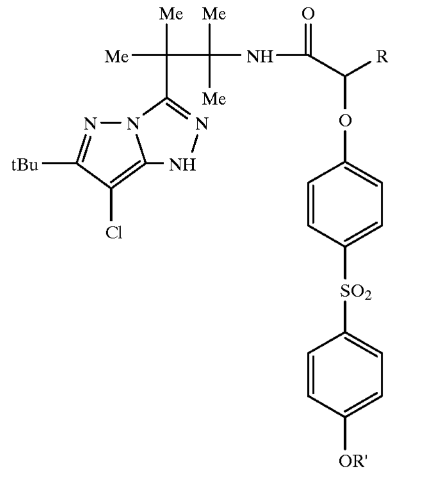

| R | R' | Melting Point |
|---|---|---|
| H | $CH_2C_6H_5$ | 204° C. |
| $CH_3$ | $CH_2C_6H_5$ | 169° C. |
| $C_2H_5$ | $CH_2C_6H_5$ | 178° C. |
| n-$C_3H_7$ | $CH_2C_6H_5$ | 182° C. |
| i-$C_3H_7$ | $CH_2C_6H_5$ | 205° C. |
| n-$C_{10}H_{21}$ | $CH_2C_6H_5$ | 130° C. |
| n-$C_{12}H_{25}$ | $CH_2C_6H_5$ | 125° C. |
| n-$C_{16}H_{33}$ | $CH_2C_6H_5$ | 118° C. |
| n-$C_{10}H_{21}$ | $CH_2CH_2OH$ | 158° C. |

By comparison, the following compounds were prepared and found to be noncrystalline:

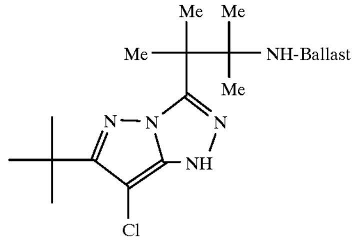

Ballast = 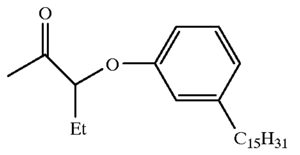

Ballast = 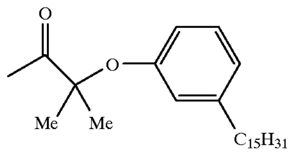

Ballast = 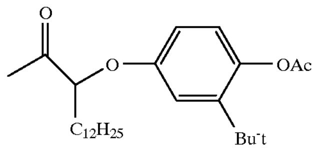

-continued

Ballast = 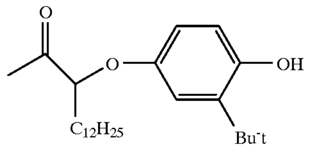

Ballast = 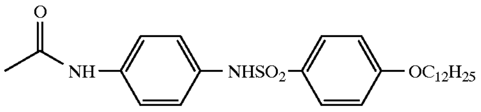

Ballast = 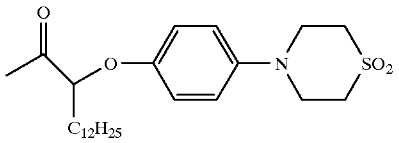

Ballast = 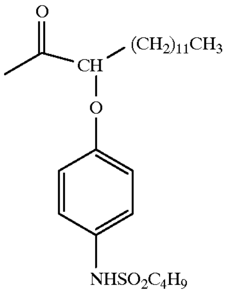

A comparison of the crystalline compounds versus the noncrystalline compounds demonstrates that ballast groups within the limitations of the invention are crystalline and therefore amenable to manufacturing in commercial quantities.

Photographic Examples

Dispersions of the couplers were prepared as described below. In one vessel, the coupler, coupler solvent, stabilizers, and ethyl acetate were combined and warmed to dissolve. To this solution was added gelatin, surfactant, and water. After manual mixing the mixture was passed three times through a Gaulin colloid mill.

The evaluation format demonstrating this invention used a constant molar laydown of image coupler (0.27 millimoles/sq.m). The levels of solvents and stabilizers incorporated in the imaging layer were included at a given weight percentage of the coupler. As the weight of the coupler laydown varied due to variation in the molecular weight of the coupler, the levels of stabilizers and solvents were adjusted to provide constant weight ratios of the solvents and stabilizers to the image coupler.

EXAMPLE 1

The photographic elements were prepared by coating the following layers in the order listed on a resin-coated paper support:

| | |
|---|---|
| 1st layer | |
| Gelatin | 3.23 g/m$^2$ |

-continued

| | |
|---|---|
| 2nd layer | |
| Gelatin | 2.15 g/m$^2$ |
| Coupler | 0.27 mmol/m$^2$ |
| Solvent S-1 | 0.88 times coupler wt. |
| Solvent S-10 (Comp 1 and 2) | 0.12 times coupler wt. |
| Solvent S-9 (Comp 3 and M-29) | 0.12 times coupler wt. |
| Stabilizer St-1 | 0.60 times coupler wt. |
| Stabilizer St-2 | 0.60 times coupler wt. |
| Stabilizer St-23 | 0.80 times coupler wt. |
| Green sensitized AgCl emulsion | 0.17 g/m$^2$ |
| 3rd layer | |
| Gelatin | 1.34 g/m$^2$ |
| 2-(2H-benzotriazol-2-yl)-4,6-bis-(1,1-dimethyl-propyl)phenol | 0.73 g/m$^2$ |
| UV-1 (Tinuvin 326, Ciba-Geigy) | 0.13 g/m$^2$ |
| Hexanoic acid, 2-ethyl-, 1,4-cyclohexanediyl bis(methylene) ester | 0.29 g/m$^2$ |
| 1,4-Benzenediol, 2,5-bis(1,1,3,3-tetamethylbutyl)- | 0.18 g/m$^2$ |
| 4th layer | |
| Gelatin | 1.40 g/m$^2$ |
| Bis(vinylsulfonylmethyl) ether | 0.14 g/m$^2$ |

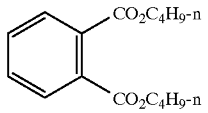

S-1

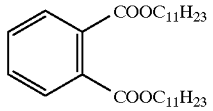

S-9

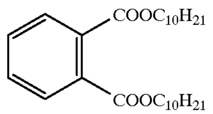

S-10

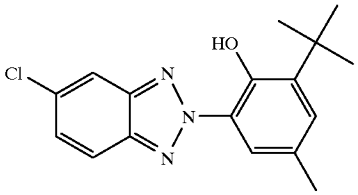

UV-1

EXPOSING AND PROCESSING OF PHOTOGRAPHIC ELEMENTS

The photographic elements were given stepwise exposures to blue light and processed as follows at 35° C.:

| | |
|---|---|
| Developer | 45 seconds |
| Bleach-Fix | 45 seconds |
| Wash (running water) | 1 minute, 30 seconds |

The developer and bleach-fix were of the following compositions:

| Developer | |
|---|---|
| Water | 700.00 mL |
| Triethanolamine | 12.41 g |
| Blankophor REU (Mobay Corp.) | 2.30 g |
| Lithium polystyrene sulfonate (30%) | 0.30 g |
| N,N-Diethylhydroxylamine (85%) | 5.40 g |
| Lithium sulfate | 2.70 g |
| N-{2-[(4-amino-3-methylphenyl) ethylamino]ethyl}methane sulfonamidesesquisulfate | 5.00 g |
| 1-Hydroxyethyl-1,1-diphosphonic acid (60%) | 0.81 g |
| Potassium carbonate, anhydrous | 21.16 g |
| Potassium chloride | 1.60 g |
| Potassium bromide | 7.00 mg |
| Water to make | 1.00 L |
| pH @ 26.7° C. adjusted to 10.04 +/− 0.05 | |

| Bleach-Fix | |
|---|---|
| Water | 700.00 mL |
| Solution of ammonium thiosulfate (54.4%) + ammonium sulfite (4%) | 127.40 g |
| Sodium metabisulfite | 10.00 g |
| Acetic acid (glacial) | 10.20 g |
| Solution of ammonium ferric ethylenediaminetetraacetate (44%) + ethylenediamine tetraacetic acid (3.5%) | 110.40 g |
| Water to make | 1.00 L |
| pH @ 26.7° C. adjusted to 5.50 +/− 0.10 | |

PHOTOGRAPHIC TESTS

Magenta dyes were formed upon processing. The following photographic characteristics were determined: $D_{max}$ (the maximum density to green light); Speed (the relative log exposure required to yield a density to green light of 1.0); and Contrast (the ratio (S-T)/0.6, where S is the density at a log exposure 0.3 units greater than the Speed value and T is the density at a log exposure 0.3 units less than the Speed value). The combination of this invention provides comparable and acceptable values for $D_{max}$, Contrast, Speed, and other photographic properties versus the check comparisons when they are coated, exposed in a controlled manner, and processed as above.

The combination of this invention also improves the light stability of the magenta dye that is formed using the conventional RA-4 process. Table I contains data on Status A density losses that are observed from processed strips when they are exposed to 50 klux intensity light for 21 days.

TABLE I

| Coupler | Fade from 1.0 | Fade from 1.7 |
|---|---|---|
| Comparison 1 | −0.30 | −0.43 |
| Comparison 2 | −0.19 | −0.29 |
| Comparison 3 | −0.26 | −0.36 |
| M-29 | −0.16 | −0.22 |

An analysis of the data shows that the magenta dye formed from the couplers of the invention are more stable to light exposure than the dye formed by the comparison couplers. Referring to the column labeled "Fade from 1.0", Comparison 1 is a currently commercially employed coupler which does not contain the required group at the 3-position. Comparison 2 contains the desired 1,1,2,2-tetramethyl configuration but does not contain the desired phenylsulfonylphenoxy group. The fade results for this coupler are respectable but this coupler does not crystallize as shown earlier under "Crystallinity Examples". Comparison 3 contains a hydroxy substituent on the remote phenyl ring. The presence of this hydroxyl group is detrimental to dye light stability.

The column labeled "Fade from 1.7" shows similar improvements for the inventive couplers when measured at this density level.

Comparison 1

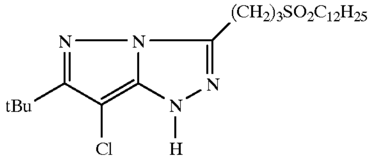

Comparison 2

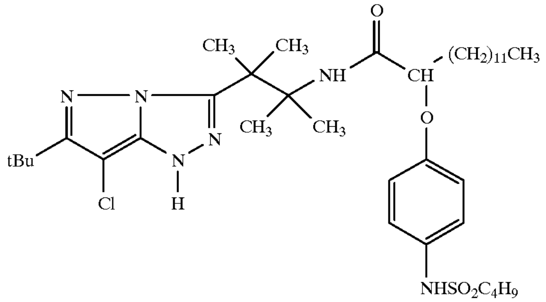

Comparison 3

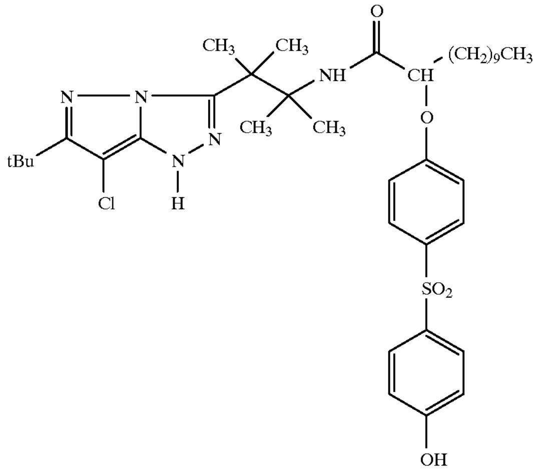

EXAMPLE 2

Photographic elements were prepared as in Example 1 with the following modifications to the levels of stabilizer:

| Sample preparation: | |
|---|---|
| First Layer | |
| Gelatin | 3.23 g/m$^2$ |
| Second Layer | |
| Gelatin | 2.15 g/m$^2$ |
| Coupler | 0.27 millimoles/m$^2$ |

-continued

| Sample preparation: | |
|---|---|
| Solvent 1 | 0.88 times coupler |
| Solvent 10 - (Comp 1 and 2) | 0.12 times coupler |
| Solvent 9 - (Comp 3 and M-29) | 0.12 times coupler |
| Stabilizer St-1 | 0.20 times coupler |
| Stabilizer St-2 | 0.20 times coupler |
| Stabilizer St-23 | 1.60 times coupler |
| Green sensitized AgCl emulsion | 0.17 g/$m^2$ |
| Third Layer | |
| Gelatin | 1.34 g/$m^2$ |
| 2-(2H-benzotriazole-2-yl)-4,6-bis-(1,1-dimethylpropyl)phenol | 0.73 g/$m^2$ |
| Tinuvin 326 ™ (Ciba-Geigy) | 0.13 g/$m^2$ |
| Hexanoic acid, 2-ethyl-1,4-cyclo-hexanediyl-bis(methylene) ester | 0.29 g/$m^2$ |
| 1,4-Benzenediol, 2,5-bis(1,1,3,3-tetramethylbutyl)- | 0.18 g/$m^2$ |
| Fourth Layer | |
| Gelatin | 1.40 g/$m^2$ |
| Bis(vinylsulfonylmethyl)ether | 0.14 g/$m^2$ |

The photographic elements were exposed, processed, and tested as previously described for Example 1. The results are shown in Table II.

TABLE II

| | 3 week 50 Klux Daylight | |
|---|---|---|
| Coupler | Fade from 1.0 | Fade from 1.7 |
| Comparison 1 | −.24 | −.37 |
| Comparison 2 | −.16 | −.24 |
| Comparison 3 | −.24 | −.34 |
| M-29 | −.15 | −.21 |

An analysis of the data shows that the magenta dye formed from the couplers of the invention are more stable to light exposure than the dye formed by the comparison couplers even though the levels of stabilizers is varied.

EXAMPLE 3

An embodiment of the invention is a multilayer element provided on a reflective support and employing silver chloride emulsions and coated as taught in *Research Disclosure*, September 1996, Item 38957 which is exemplified by the following:

| Coating Format | Laydown mg/$m^2$ |
|---|---|
| Layer Blue Sensitive Layer | |
| Gelatin | 1300 |
| Blue sensitive silver | 640 |
| Y-1 | 440 |
| St-24 | 440 |
| S-1 | 190 |
| Layer Interlayer | |
| Gelatin | 650 |
| Sc-2 | 55 |
| S-1 | 160 |
| Layer Green Sensitive Layer | |
| Gelatin | 1100 |
| Green sensitive silver | 70 |
| M-29 | 270 |
| S-1 | 75 |
| S-3 | 32 |

-continued

| | |
|---|---|
| St-2 | 20 |
| St-1 | 165 |
| St-23 | 530 |
| Layer UV Interlayer | |
| Gelatin | 635 |
| UV-1 | 30 |
| UV-2 | 160 |
| Sc-2 | 50 |
| S-4 | 30 |
| S-1 | 30 |
| Layer Red Sensitive Layer | |
| Gelatin | 1200 |
| Red sensitive silver | 170 |
| C-1 | 365 |
| S-1 | 360 |
| UV-2 | 235 |
| S-5 | 30 |
| Sc-2 | 3 |
| Layer UV Overcoat | |
| Gelatin | 440 |
| UV-1 | 20 |
| UV-2 | 110 |
| Sc-2 | 30 |
| S-4 | 20 |
| S-1 | 20 |
| Layer SOC | |
| Gelatin | 490 |
| Sc-2 | 17 |
| $SiO_2$ | 200 |
| Surfactant | 2 |

C-1

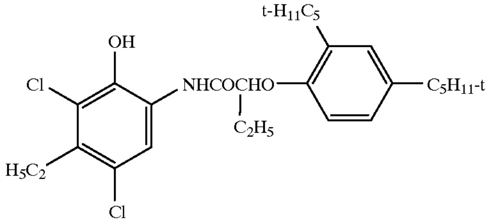

S-4

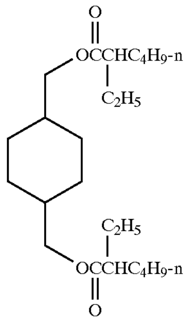

S-5 $CH_3COOC_2H_4OC_2H_4OC_4H_9$

Sc-2

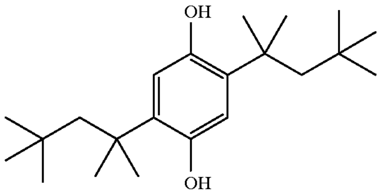

St-24 N-t-butyl(acrylamide)/n-butyl acrylate copolymer (50:50)

-continued

UV-2

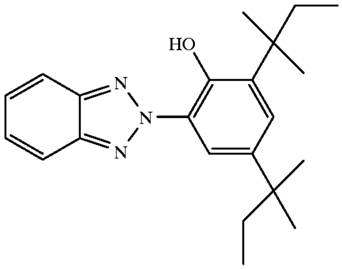

Y-1

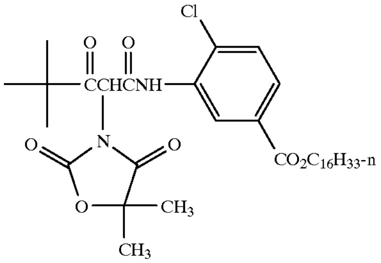

The entire contents of all copending applications, patents, and other publications cited in this specification are incorporated herein by reference.

What is claimed is:

1. A photographic element comprising a silver halide emulsion layer having associated therewith a dye-forming coupler represented by Formula I:

I

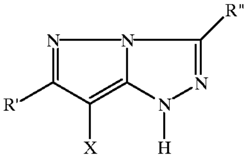

wherein

X is hydrogen or a coupling-off group; and

R' is a tertiary alkyl group and R" represents the group

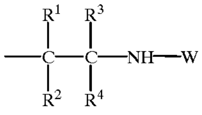

in which $R^1$, $R^2$, and $R^3$ are independently selected alkyl groups, provided that any two of $R^1$, $R^2$ and $R^3$ may join to form a ring;

$R^4$ is hydrogen or a substituent, provided that $R^3$ and $R^4$ may join to form a ring when $R^4$ is a substituent; and W is a substituent having the formula:

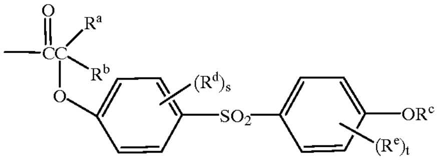

wherein $R^a$ and $R^b$ are independently selected from the group consisting of hydrogen, and alkyl or aryl groups;

$R^c$ is a substituent;

each $R^d$ and $R^e$ is an independently selected substituent with s and t being independently selected integers from 0 to 4.

2. The element of claim 1 wherein R' is selected from the group consisting of a t-butyl group, a 1-methyl-1-cyclopropyl group, a t-pentyl group, a t-octyl group, and an adamantyl group.

3. The element of claim 1 wherein X is hydrogen, a halogen, or an aryloxy group.

4. The element of claim 3 wherein X is chloro.

5. The element of claim 1 wherein $R^1$, $R^2$, and $R^3$ are each alkyl groups of 6 carbons or less.

6. The element of claim 5 wherein $R^1$, $R^2$, and $R^3$ are each selected from the group consisting of methyl, ethyl, cyclopentyl, and cyclohexyl groups.

7. The element of claim 5 wherein $R^1$ and $R^2$ join to form a ring.

8. The element of claim 1 wherein $R^4$ is selected from the group consisting of hydrogen, methyl and ethyl groups.

9. The element of claim 1 wherein $R^3$ and $R^4$ join to form a ring.

10. The element of claim 8 wherein $R^1$ and $R^3$ join to form a ring.

11. The element of claim 1 wherein at least one of $R^a$ and $R^b$ contains at least 6 carbon atoms.

12. The element of claim 11 wherein at least one of $R^a$ and $R^b$ is an alkyl group of least 6 carbon atoms.

13. The element of claim 1 wherein $R^c$ is an alkyl group.

14. The element of claim 13 wherein $R^c$ is an aralkyl group.

15. The element of claim 13 wherein $R^c$ contains at least 6 carbon atoms.

16. The element of claim 1 wherein $R^c$ is a phenylmethylene group.

17. The element of claim 1 wherein R' is t-butyl and $R^1$ through $R^4$, $R^a$, and $R^c$ are alkyl groups.

18. The element of claim 17 wherein $R^1$ through $R^4$ are methyl groups.

19. The element of claim 18 wherein $R^c$ is a phenyl methylene group.

20. The element of claim 1 wherein the element is provided on a reflective support.

21. The element of claim 1 containing a dye light stabilizer in the same layer as the dye-forming coupler represented by formula I.

22. The element of claim 21 wherein the stabilizer is selected from the group consisting of:

St-I

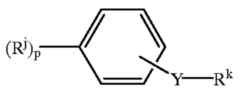

St-II

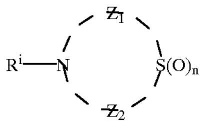

and

St-III

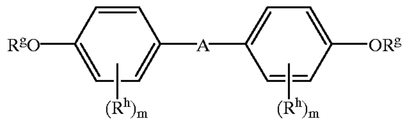

wherein:

each $R^g$ independently represents a hydrogen atom, an alkyl group, an alkenyl group or an aryl group;

each $R^h$ independently represents a halogen atom, an alkyl group, an alkenyl group an alkoxy group, an aryl group, an aryloxy group, an alkylthio group, an aryl thio group, an acyl group, an acylamino group, a sulfonyl group, a sulfonamide group or a hydroxy group;

each m is, individually an integer of 0 to 4; and

A represents an alkylene group having 1 to 6 carbon atoms in its linear structure, $R^i$ represents an aryl group or a heterocyclic group;

$Z_1$ and $Z_2$ each represent an alkylene group having 1 to 3 carbon atoms provided that the total number of carbon atoms in the ring is 3 to 6;

n is an integer of 1 or 2;

each $R^j$ is independently alkyl or alkoxy of 1 to 32 carbon atoms;

p is an integer of 1 to 4 and when p is greater than 1, only one $R^j$ is alkoxy;

Y is —$NHSO_2$— or —$SO_2NH$—; and $R^k$ is an alkyl group of 1 to 16 carbon atoms.

23. The element of claim 22 wherein the stabilizer is represented by formula St-I.

24. The element of claim 23 wherein there are present stabilizers represented by both formulas St-I and St-II.

25. The element of claim 24 wherein there are present stabilizers represented by all three formulas St-I, St-II, and St-III.

26. The element of claim 21 wherein the stabilizer is represented by a formula selected from the group consisting of:

St-1

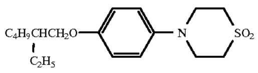

-continued

St-2

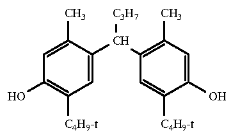

St-3

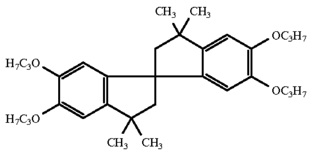

St-4

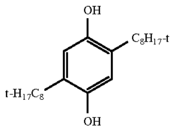

St-5

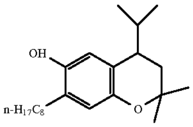

St-6

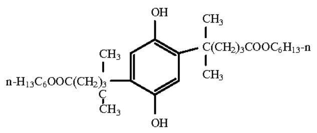

St-7

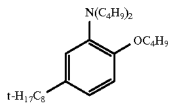

St-8

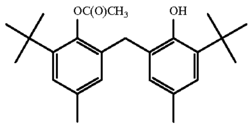

St-9

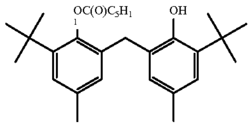

St-10

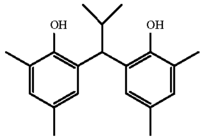

St-11

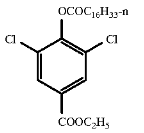

-continued
St-12
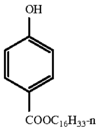
St-13
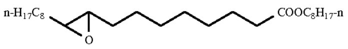
St-14
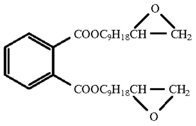
St-15
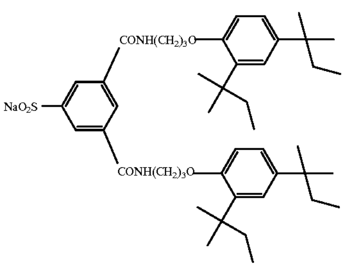
St-16
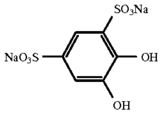
St-17
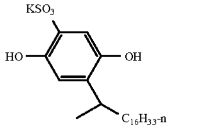
St-18
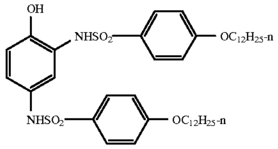
St-19
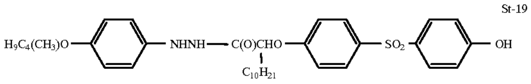
St-20
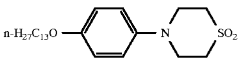
St-22
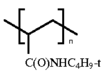
n = 75-8,000
and
-continued
St-23
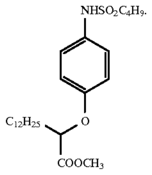
27. The element of claim 1 wherein the emulsion layer containing the coupler of Formula I is sensitized to green light and the coupler is a magenta dye-forming coupler.
28. The element of claim 1 wherein the dye-forming coupler of Formula I is selected from the group consisting of:
M-1
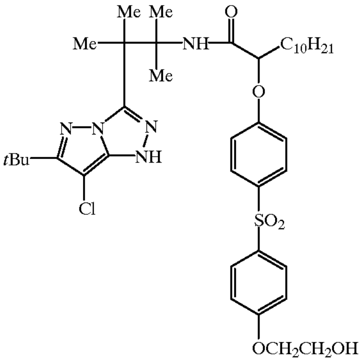
M-2
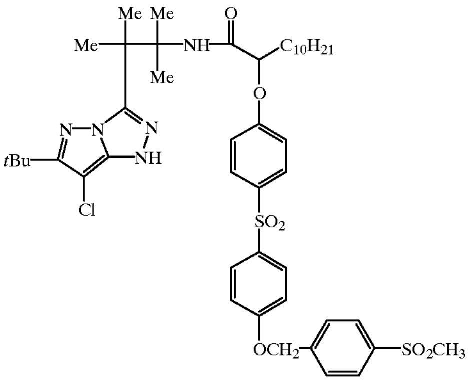
M-3
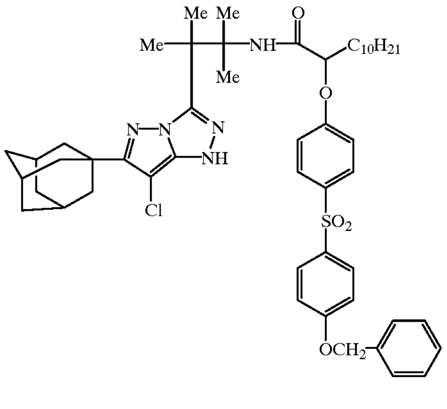

-continued
M-4
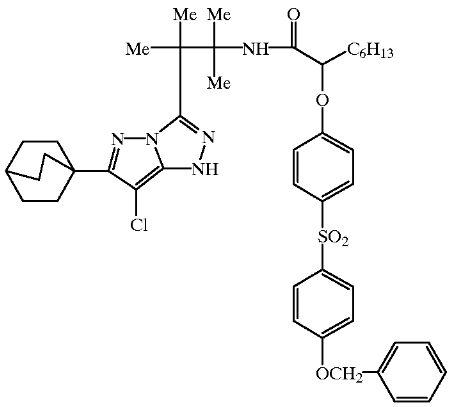
M-5
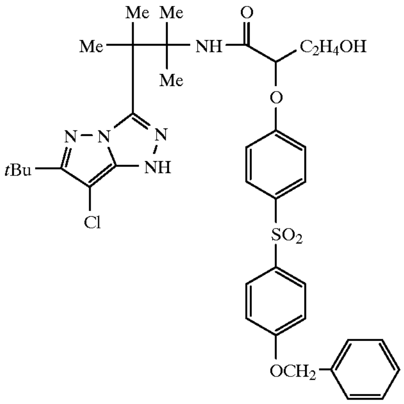
M-6
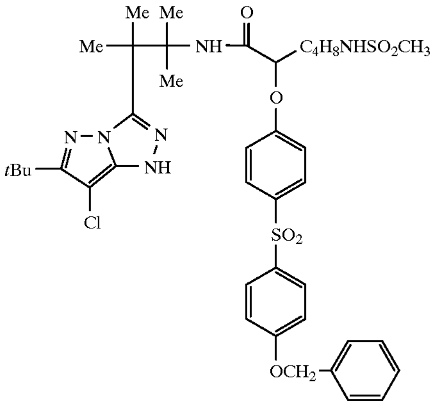
-continued
M-7
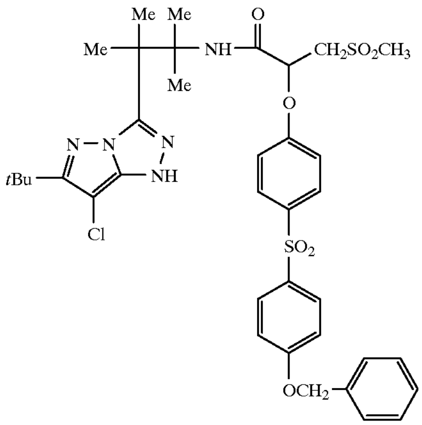
M-8
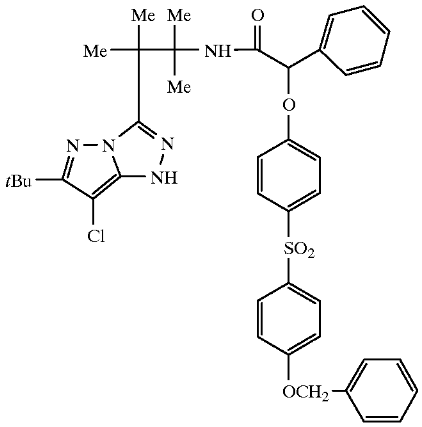
M-9
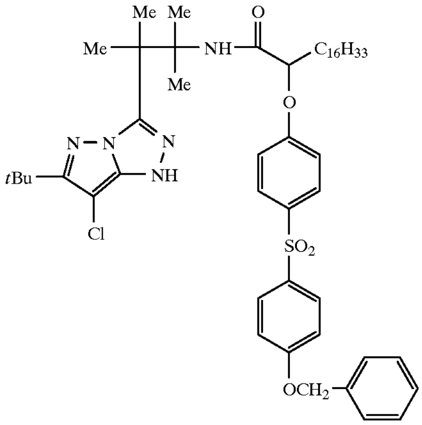

-continued
M-10
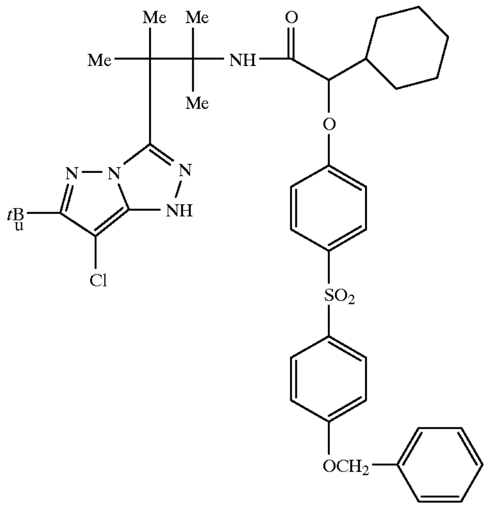
M-11
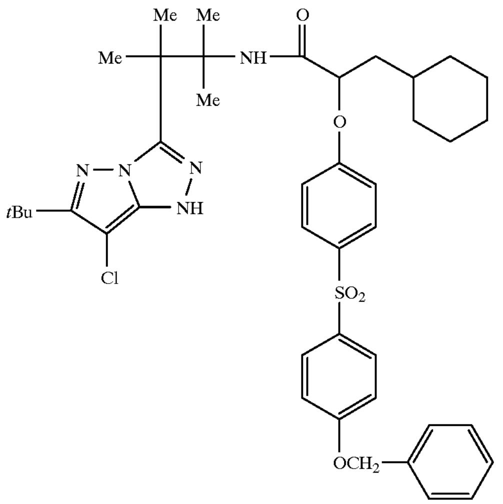
M-12
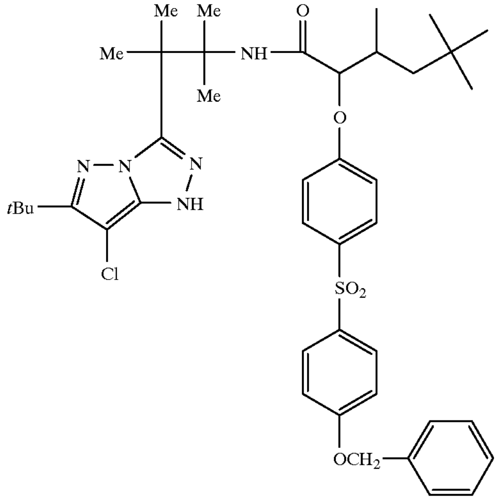
-continued
M-13
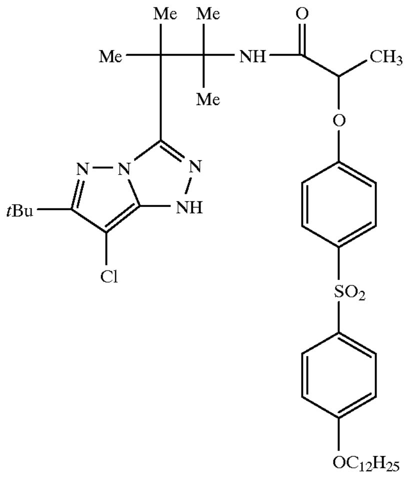
M-14
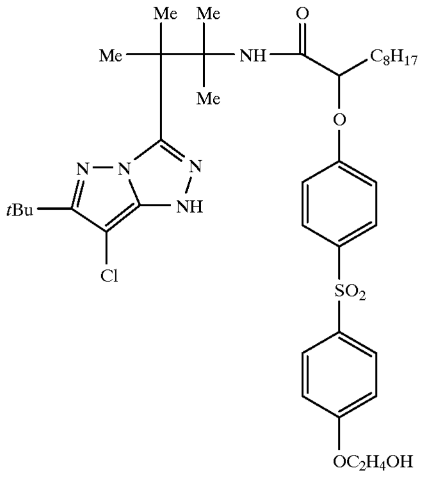
M-15
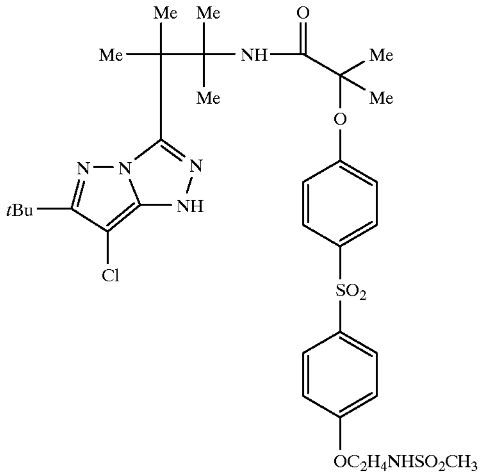

-continued
M-16
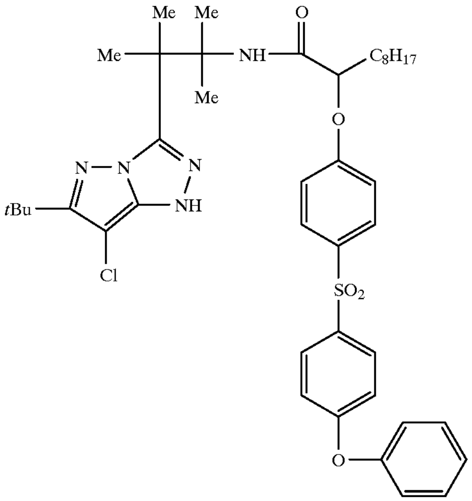
M-17
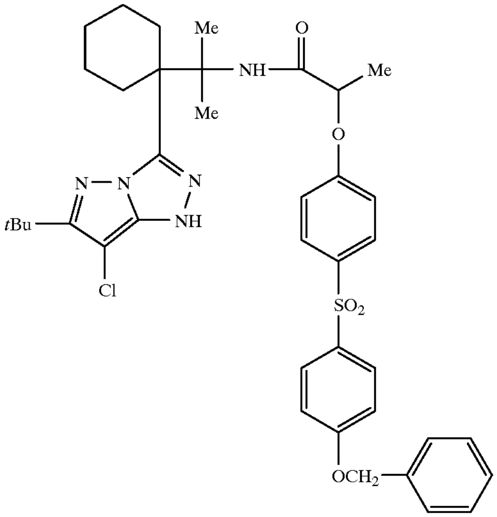
M-18
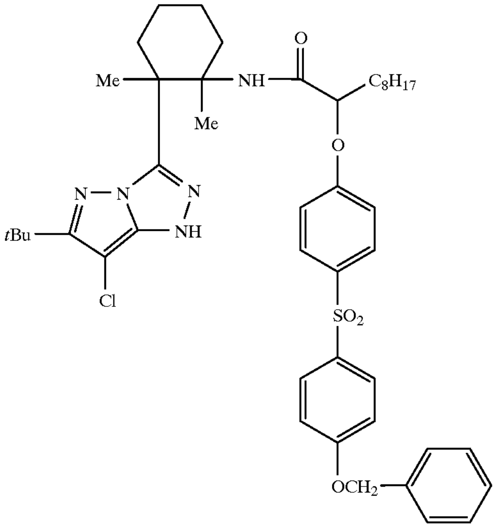
-continued
M-19
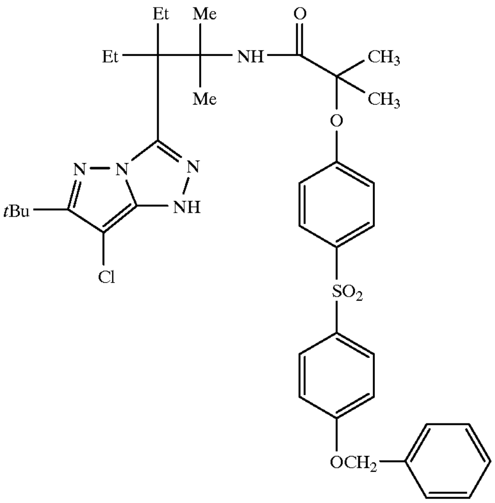
M-20
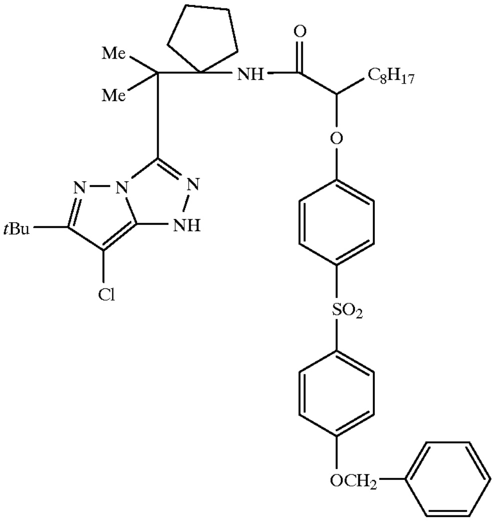
M-21
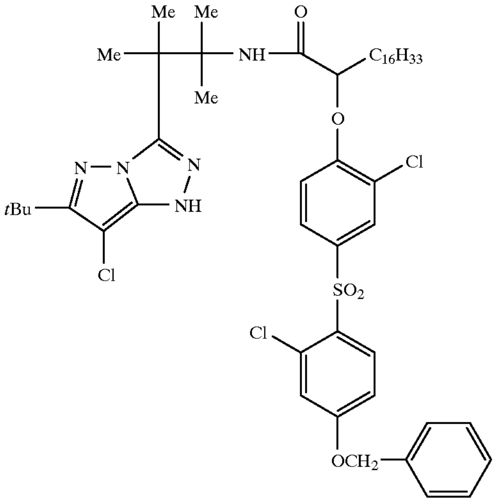

-continued
M-22
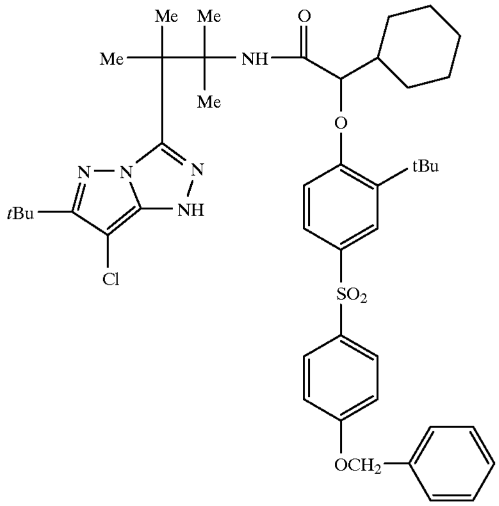
M-23
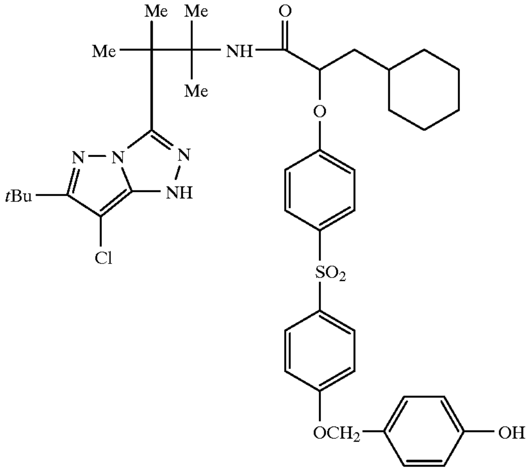
M-24
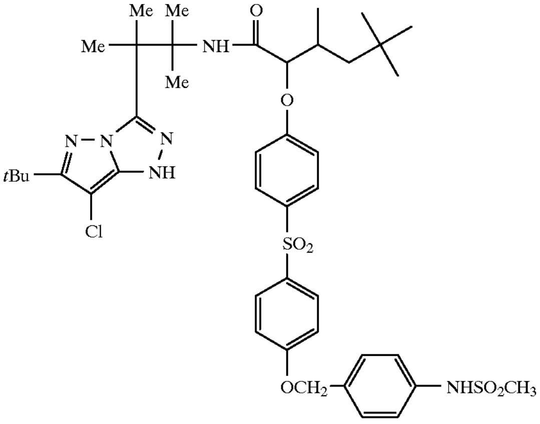
-continued
M-25
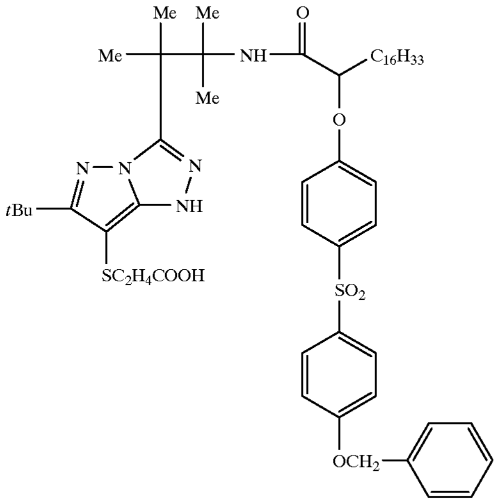
M-26
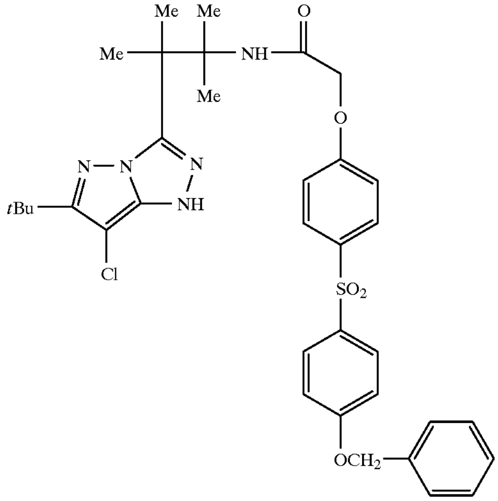
M-27
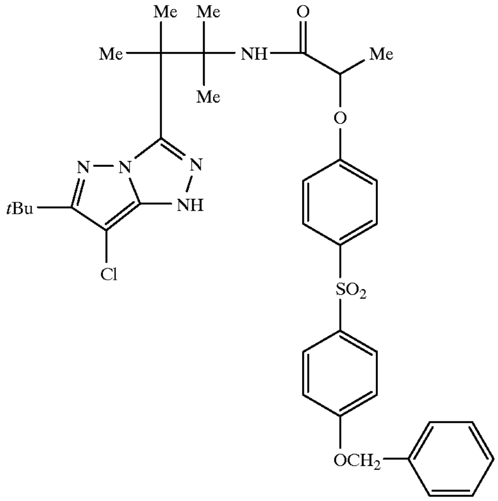

-continued
M-28
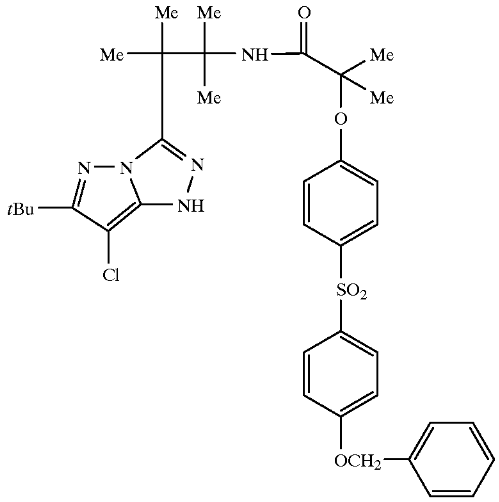
M-29
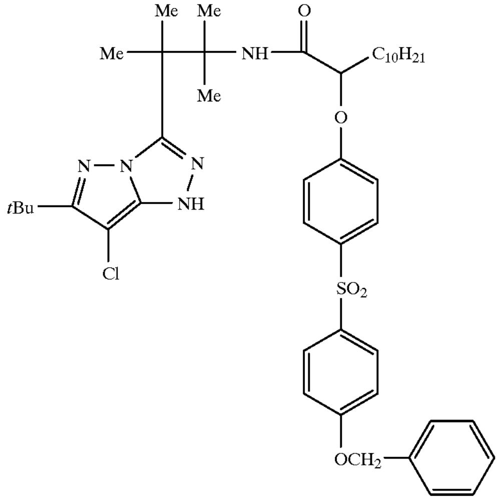
M-30
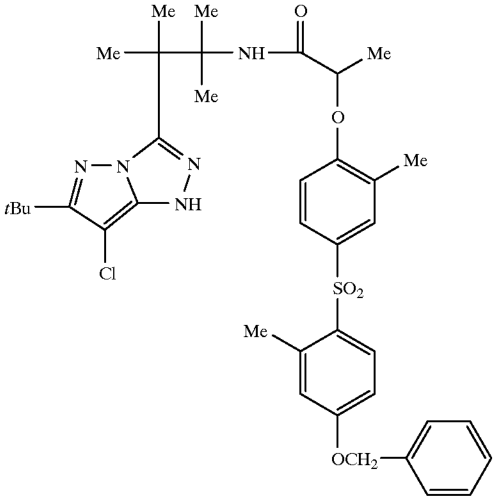
-continued
M-31
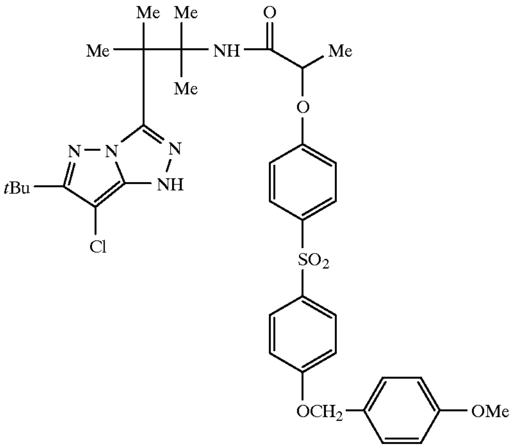
M-32
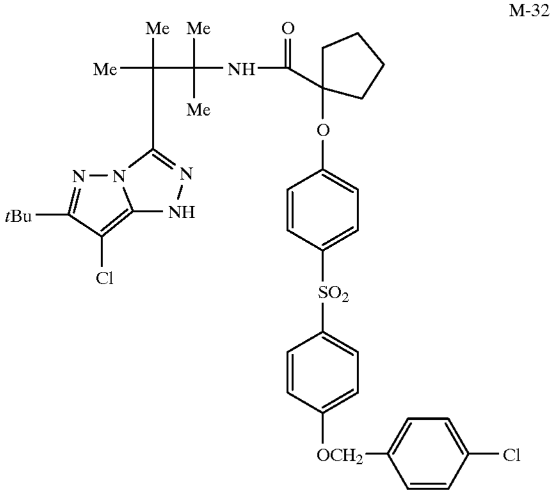
M-33
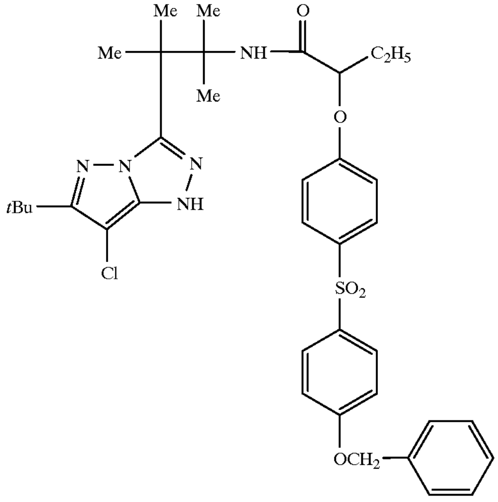

-continued
M-34
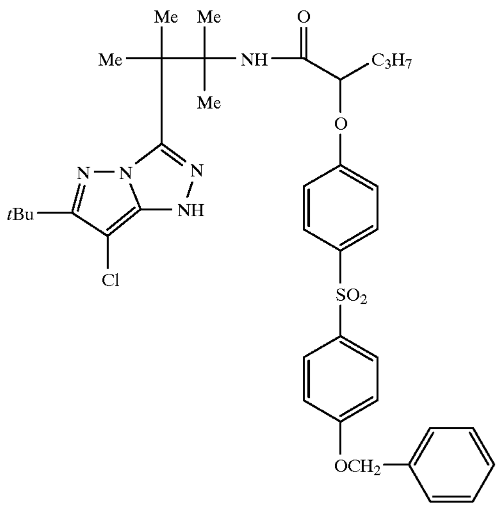
M-35
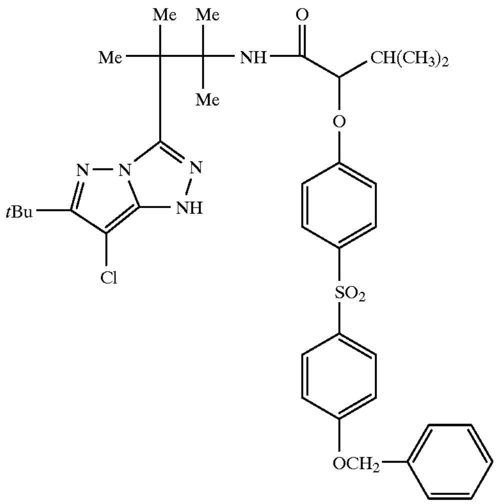
and
-continued
M-36
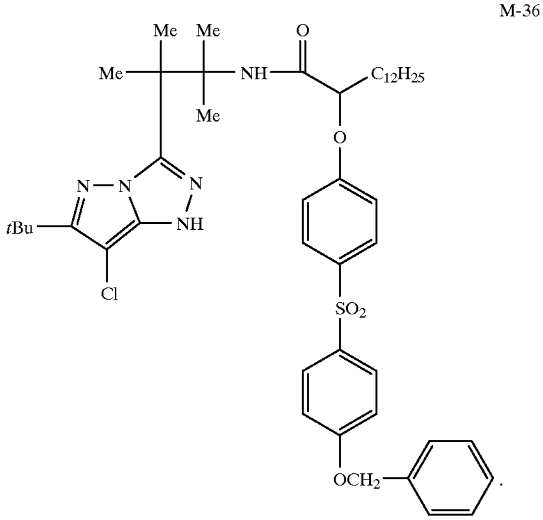
29. The element of claim 1 wherein the dye-forming coupler has the formula:
M-29
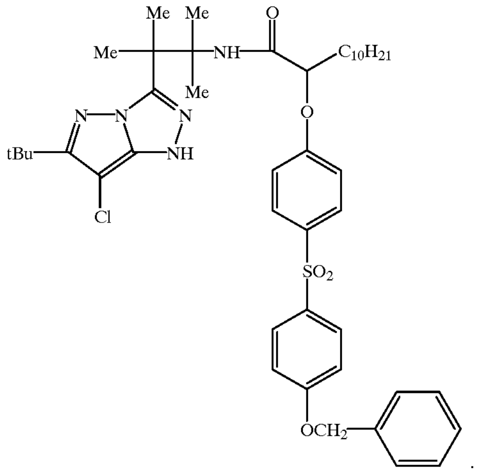
30. A process for forming an image in an element as described in claim 1 after the element has been imagewise exposed to light comprising contacting the exposed element with a color developer.
* * * * *